United States Patent [19]

Musters et al.

[11] Patent Number: 5,591,620

[45] Date of Patent: Jan. 7, 1997

[54] METHODS OF DETECTING AND ISOLATING A RIPENING FORM OF A POLYPEPTIDE HAVING RHAMNOGALACTURONASE ACTIVITY

[75] Inventors: Wouter Musters, Maassluis; Hein Stam, Diemen; Maria E. Suykerbuyk, Utrecht; Jacob Visser, Wageningen; Johannes M. Verbakel, Maasland, all of Netherlands

[73] Assignee: Unilever Patent Holdings, B.V., Vlaardingen, Netherlands

[21] Appl. No.: 536,242

[22] Filed: Sep. 29, 1995

Related U.S. Application Data

[62] Division of Ser. No. 61,062, May 14, 1993.

[30] Foreign Application Priority Data

May 15, 1992 [EP] European Pat. Off. .............. 92201403

[51] Int. Cl.⁶ ...................................................... C12N 9/26
[52] U.S. Cl. ........................... 435/201; 435/183; 435/7.1
[58] Field of Search ........................... 435/201, 7.1, 183; 514/57; 536/8; 426/271, 330.5

[56] References Cited

FOREIGN PATENT DOCUMENTS 9219728  11/1992  WIPO ............................. C12N 9/24

OTHER PUBLICATIONS

Bio Speparations 1: pp. 97–110, (1990) Ehle, H. et al.
Plant Physiol. 102(1 Suppl) (1993) p. 46, Chen, H et al.
Carbohydrate Research, 206, (1990) pp. 131–144, Colquhoun, I. J.
J. Cell Biochem, Suppl 0(17 Part A), (1993) p. 15, Mutter et al.
Hortscience 27(6) (1992) p. 653, Kim, J. et al.
Sakamoto, T. et al, Biosci, Biotech, Biochem, 57(1i) pp. 1832–1837, 1993.
Schols, H. A. et al, Carbohydrate Research, 206(1990) pp. 105–115.
Schols et al., "Rhamnogalacturonase: a novel enzyme that degrades the hairy regions of fruit pectins", Carbohydrate Research, Elsevier Science Publishers B. V., Amsterdam, 206(1990), pp. 105–115.
Schols et al, "Structural features of hairy regions of pectins isolated from apple juice produced by the liquification process", Carbohydrate Research, Elsevier Science Publishers B.V., Amsterdam, 206 (1990), pp. 117–129.
deRuiter et al, "Identification by n.m.r. spectroscopy of oligosaccharides obtained by treatment of the hairy regions of apple pectin with rhamnogalacturonase", Caroydydrate Research, Elsevier Science Publishers B.V., Amsterdam, 206 (1990), pp. 131–144.
Uitzetter et al, "Characterization of *Aspergillus nidulas* Mutants in Carbon Isolated after D–Galacturonate Enrichment", Journal of General Microbiology (1986), vol. 132, pp. 1167–1172.

Burnette, W. Neal, "Western Blotting: Electrophoretic Transfer of Proteins from Dodecyl Sulfate–Poly–Acrylamide Gels to Unmodified Nitrocellulose and Radiographic Detection with Antibody and Radioiodinated Protein A", Analytical Biochemistry, vol. 112, pp. 195–202 (1981).
Veen et al, "Induction purification and characterization of arabinases produced by *Aspergillus niger*", Arch. Microbiol, Springer–Verlag 1991, vol. 157, pp. 23–28.
Ishii et al, "Susceptibility of Fruit Juice to Enzymatic Clarification by Pectin Lyase and Its Relation to Pectin in Fruit Juice", J. Agr. Food Chem., vol. 21, No. 2, 1973, pp. 269–272.
Voragen et al, "Enzymatische Modifcatie van Polysaccharaiden", Biotechnologie, VMT, 14 Jun., 1990, No. 12, pp. 22–24.
Punt et al, "Transformation of Aspergillis based on the hygromycin B resistance marker from *Escherida coli*", Gene, 56, 1987, Elsevier Science Publishers B.V., pp. 117–124.
Voragen et al, "Food Enzymes" Prospects and Limitations, Dept of Food Science, Agri. University, Wageningen, The Netherlands.
W. Pilnik, "Enzymes in the Beverage Industry", Dept of Food Science, Agri. University, Wageningen, The Netherlands.
Maldonado et al, "Catabolite Repression of the Synthesis of Inducible Polygalacturonase and Pectinesterase by *Aspergillis niger* sp.", Current Microbiology, vol. 18 (1989), pp. 303–306.
Vishniac et al, "The Thiobacilli", Dept. of Microbiology, vol. 21 (1957), Yale University, New Haven, Connecticut, pp. 195–213.
McNeil et al, "Structure and Function of the Primary Cell Walls of Plants", Ann. Rev. Biochem. vol. 53 (1984), pp. 625–663.
Aitken et al, "Peptide preparation and characterization".
Goosen et al, "Transformation of *Aspergillus niger* using the homologous orotidine–5–phosphate–decarboxylase gene", Current Genetics, vol. 11 (1987), Agricalatural Univ., Wageningen, The Netherlands, pp. 499–503.

(List continued on next page.)

Primary Examiner—James C. Housel
Assistant Examiner—Ginny Allen Portner
Attorney, Agent, or Firm—Cushman Darby & Cushman, L.L.P.

[57] ABSTRACT

The invention relates to isolation of an Aspergillus gene encoding rhamnogalacturonase (RG-ase) and the construction of recombinant Aspergillus strains with overexpression of RG-ase. These strains can be used for the commercial production of RG-ase. RG-ase is an important enzyme in processes requiring the degradation and/or modification of pectin or modification of pectin-containing vegetable or plant cell wall material. RG-ase may be used in various applications, including the processing of fruits and vegetables, in the extraction of components from vegetable material or for improving the functionality of pectin or pectin-containing vegetable material, food material or plant cell wall material.

4 Claims, 28 Drawing Sheets

OTHER PUBLICATIONS deGraaff et al, "Isolation and transformation of the pyruvate kinase gene of *Aspergillus nidulans*", Current Genetics, Agricultural Univ. vol. 13 (1988), Wageningen, The Netherlands, pp. 316–321.

Gysler et al, "Isolation and Structure of the Pectin Lyase D–Encoding Gene from *Aspergillus niger*", Gene 03474, Elsevier Science Publishers (1990) pp. 101–108.

Glover, Gene Cloning: The Mechanics of DNA Manipulation—1985—Printed in Great Britain at the University Press, Cambridge (ISBN 0 412 26600 8 (HB)) pp. 1–20.

Fig. 3.

CNBr fragment#7  (Met)-Asp-Thr- ? -Ser-Asp-Gly-Glu-Val-Tyr-Asn- ?

CNBr fragment#15 (Met)-Ala-Ile-Arg-Gly-Gly-Asn-Glu-Gly-Gly-Leu-Asp-Gly-Ile-Asp-Val-Asn?

Elys fragment#7  (Lys)-Asp-Ser-?-?-His-Thr-?- Tyr-Ser-Thr-?-?-?-Val-?-Ala-Ala-Pro-?-Gly-Tyr-?-Ala-?-?-Met-Ala-?-?-Leu-?-?-Ala-Phe-Gly-Leu-?-Ala-?

Elys fragment#5  (Lys)-Thr-?-Asn-Ile-Leu-Ser-Tyr-Gly_Ala-Val-Ala-Asp-?-Ser-Thr-Asp-Val-Gly-Pro-?

```
GAATTCGGCA CGAGTGCTCC CATTGATTCA AGTGAATC ATG CGT GCT CTT TTC     53
                                          Met Arg Ala Leu Phe
                                          -18             -15

CTT CTT GCG CTG GGT TCT ATC CCG GCG CTC GTC AGC GGT CAA CTC TCT   101
Leu Leu Ala Leu Gly Ser Ile Pro Ala Leu Val Ser Gly Gln Leu Ser
        -10                  -5                           1

GGC AGT GTT GGC CCC TTG ACC TCT GCT TCC ACC AAA GGT GCG ACA AAA   149
Gly Ser Val Gly Pro Leu Thr Ser Ala Ser Thr Lys Gly Ala Thr Lys
      5                      10                      15

ACA TGC AAT ATC CTC AGC TAC GGC GCA GTG GCC GAC AAC TCG ACC GAT   197
Thr Cys Asn Ile Leu Ser Tyr Gly Ala Val Ala Asp Asn Ser Thr Asp
    20                      25                      30         35

GTT GGG CCT GCC ATT ACA TCG GCC TGG GCT GCA TGC AAG AGC GGA GGT   245
Val Gly Pro Ala Ile Thr Ser Ala Trp Ala Ala Cys Lys Ser Gly Gly
              40                      45                      50

CTT GTC TAC ATC CCA TCT GGC AAC TAT GCC TTA AAC ACC TGG GTC ACC   293
Leu Val Tyr Ile Pro Ser Gly Asn Tyr Ala Leu Asn Thr Trp Val Thr
          55                      60                      65
```

Fig. 6B

```
CTG ACT GGA GGC AGT GCG ACC GCA ATC CAG CTG GAT GGT ATC ATT TAT    341
Leu Thr Gly Gly Ser Ala Thr Ala Ile Gln Leu Asp Gly Ile Ile Tyr
                 70                  75                  80

CGC ACA GGT ACC GCC AGT GGG AAC ATG ATT GCA GTC ACT GAC ACC ACC    389
Arg Thr Gly Thr Ala Ser Gly Asn Met Ile Ala Val Thr Asp Thr Thr
         85                  90                  95

GAC TTC GAG CTG TTC AGT AGC ACC TCC AAA GGT GCT GTG CAG GGA TTC    437
Asp Phe Glu Leu Phe Ser Ser Thr Ser Lys Gly Ala Val Gln Gly Phe
100                 105                 110                 115

GGC TAT GTG TAC CAT GCG GAG GGA ACC TAC GGA GCA CGG ATT CTG CGC    485
Gly Tyr Val Tyr His Ala Glu Gly Thr Tyr Gly Ala Arg Ile Leu Arg
         120                 125                 130

TTG ACT GAT GTG ACC CAT TTC TCT GTG CAT GAT GTG ATC TTG GTG GAT    533
Leu Thr Asp Val Thr His Phe Ser Val His Asp Val Ile Leu Val Asp
                135                 140                 145
```

Fig. 6C

```
GCG CCT GCT TTC CAC TTT ACC ATG GAT ACC TGC TCC GAT GGG GAG GTG    581
Ala Pro Ala Phe His Phe Thr Met Asp Thr Cys Ser Asp Gly Glu Val
150                             155                 160

TAC AAC ATG GCG ATT CGT GGT GGC AAT GAG GGC GGC TTG GAC GGG ATT    629
Tyr Asn Met Ala Ile Arg Gly Gly Asn Glu Gly Gly Leu Asp Gly Ile
165                 170                 175

GAT GTC TGG GGA AGC AAC ATC TGG GTT CAC GAT GTT GAA GTG ACC AAC    677
Asp Val Trp Gly Ser Asn Ile Trp Val His Asp Val Glu Val Thr Asn
180                 185                 190                 195

AAG GAT GAA TGT GTA ACA GTC AAG AGC CCG GCC AAC AAT ATT CTG GTG    725
Lys Asp Glu Cys Val Thr Val Lys Ser Pro Ala Asn Asn Ile Leu Val
                200                 205                 210

GAG AGC ATC TAT TGC AAC TGG AGT GGT TGC GCA ATG GGG TCG CTC        773
Glu Ser Ile Tyr Cys Asn Trp Ser Gly Cys Ala Met Gly Ser Leu
215                 220                 225
```

Fig. 6D

```
GGG GCC GAC ACC GAC GTC ACC GAT ATT GTC TAC CGC AAT GTT TAC ACC    821
Gly Ala Asp Thr Asp Val Thr Asp Ile Val Tyr Arg Asn Val Tyr Thr
230                     235                 240

TGG TCA TCG AAC CAG ATG TAC ATG ATC AAG AGC AAT GGC GGT AGT GGA    869
Trp Ser Ser Asn Gln Met Tyr Met Ile Lys Ser Asn Gly Gly Ser Gly
245                 250                 255

ACG GTG TCG AAT GTT TTG CTG GAA AAT TTC ATC GGG CAC GGT AAT GCG    917
Thr Val Ser Asn Val Leu Leu Glu Asn Phe Ile Gly His Gly Asn Ala
260                 265                 270                 275

TAC TCG CTC GAC ATC GAC GGC TAC TGG AGC AGC ATG ACT GCG GTG GCC    965
Tyr Ser Leu Asp Ile Asp Gly Tyr Trp Ser Ser Met Thr Ala Val Ala
                280                 285                 290

GGG GAC GGG GTG CAG CTG AAC AAC ATC ACG GTG AAG AAC TGG AAG GGC    1013
Gly Asp Gly Val Gln Leu Asn Asn Ile Thr Val Lys Asn Trp Lys Gly
            295                 300                 305
```

Fig. 6E

```
ACC GAG GCG AAC GGA GCG ACC CGA CCA CCG ATC CGA GTG GTG TGT AGT    1061
Thr Glu Ala Asn Gly Ala Thr Arg Pro Pro Ile Arg Val Val Cys Ser
310                 315                 320

GAC ACG GCG CCT TGC ACG TTG ACG GAC CTG GAA GAC ATT GCC ATC TGG    1109
Asp Thr Ala Pro Cys Thr Leu Thr Asp Leu Glu Asp Ile Ala Ile Trp
        325                 330                 335

ACC GAA AGC GGC TCG AGT GAA CTG TAC CTG TGC CGT TCC GCT TAC GGA    1157
Thr Glu Ser Gly Ser Ser Glu Leu Tyr Leu Cys Arg Ser Ala Tyr Gly
340                 345                 350                 355

TCG GGA TAC TGT TTG AAG GAC AGC TCT TCG CAC ACA TCC TAC ACC ACA    1205
Ser Gly Tyr Cys Leu Lys Asp Ser Ser His Thr Ser Tyr Thr Thr
        360                 365                 370

ACC AGC ACT GTC ACG GCG GCT CCC TCA GGA TAT TCG GCG ACA ACC ATG    1253
Thr Ser Thr Val Thr Ala Ala Pro Ser Gly Tyr Ser Ala Thr Thr Met
375                 380                 385
```

Fig. 6F

```
GCA GCC GAC TTG GCA ACC GCA TTT GGT CTC ACT GCT TCC ATT CCC ATT    1301
Ala Ala Asp Leu Ala Thr Ala Phe Gly Leu Thr Ala Ser Ile Pro Ile
            390                 395                 400

CCG ACC ATC CCG ACC TCG TTT TAT CCC GGG TTG ACC CCG TAC AGT GCC    1349
Pro Thr Ile Pro Thr Ser Phe Tyr Pro Gly Leu Thr Pro Tyr Ser Ala
            405                 410                 415

TTG GCA GGC TAGTAGGTGT GAAAGCAAGG TGGGATTGAT GTGTCACCGT            1398
Leu Ala Gly
420

CGCAGTGGAA GGAATGTCGG GAGAAGGAGA AGGAGAAGGA GAAGGAGAAG GAGGAGAGAT   1458

CGTTGAATCG TTGAGTCGTT GAGTCGTTGA GATCATGGAT CAGGCTGGTA ATCGTTACCT   1518

CACGATTCCG TAGGTGTTTG TAAGTAAGTA TGTATGTTAT ATCAATCAAA AGGAAGATCC   1578

TCCTTCGAAA AAAAAAAAAA AAAAAAACTC GAG                               1611
```

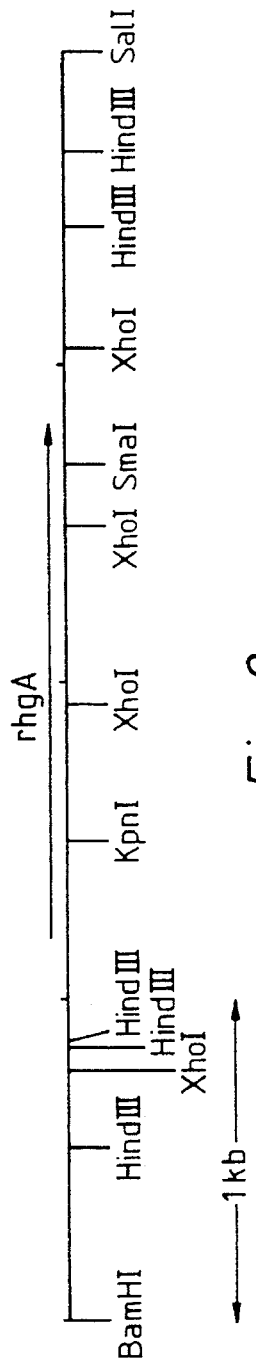
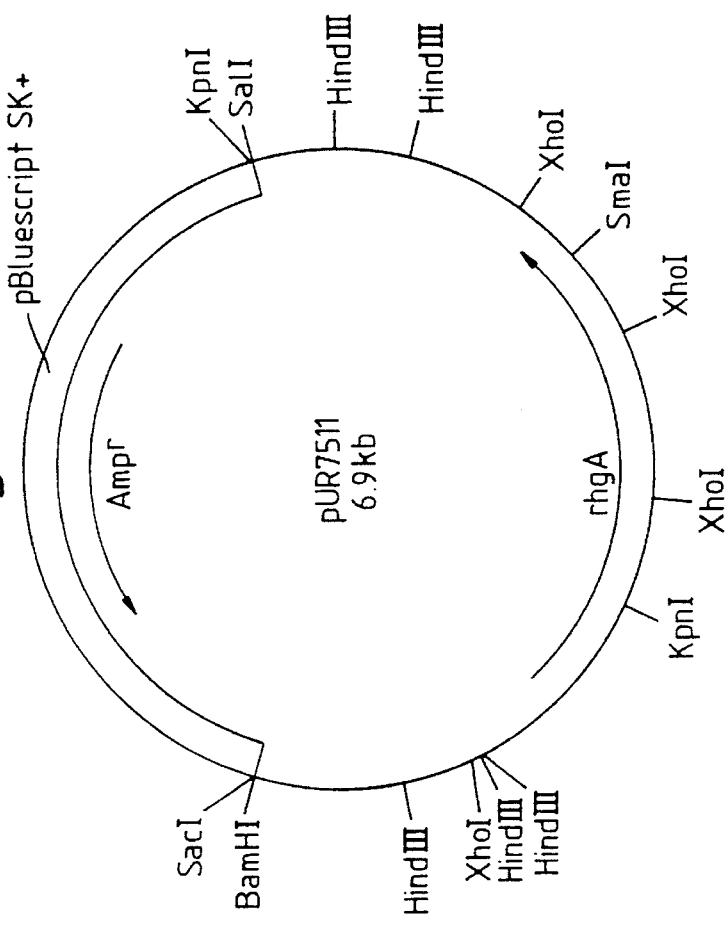
Fig. 7.
Fig. 8.

Fig.9A

```
GGATCCCTGC AGAATCGCTG TGGAGTATAC CTCGCTTTCT AGGACTGCTG ATGGGTGAAA    60
TACCGCGTCC TGAGAGATGA CGAGAATGGC TATGGGCCAC GGGGTAAAGG GTTCATTGAT   120
CATGTCGATA TTCCAGAGAG CGTTGAGCGA GCGTTTCATG GCTTAGAGCC CGGGATACTA   180
GGATCGGAAC TAGCCAAGAG ATGACTCTGA TTGGTCAAAG CTTGCTCTTT AGATTATCTT   240
CAAGACTATT TCGACTCTTC ATAATATGGT AGTCCCCAGG ATAGTACAGC TATCGTAGGC   300
AGAGTGCCCT GACGAAACGA TGACGACATT CTGTATTACT CGGTTATCAA ATGCGGACAC   360
AGGCGTCAAA TATCAAGCGA CTTTGGCGTC GCGAATGTGA TGCTGGGCCG TCTTGGTAGG   420
GCCTGAGCGC TGGGTGCAAC ACGAAGAACA CAACCGGCAC GTAACCCACT GGTACTCGG    480
CCGTCACTCA CCCGACAGCT GCTCTTGAAC AATGTCTTCT TTCCTGCTCG CATCAAATCA   540
ACCCGGAATT TCAGGGCAGA AGCTTTATGG TGATTGCTTG TTGCATGCAT CACCCCGCCG   600
CACGTACCCC ACAAAGTCAT CAGGCGATGC ATCTAGCTGA GGGGATGAG TTCCTGTTTG   660
ACATTTGCCG AGATGAACCC TCCTAGCCGC CCCTGGAACT AAATCCCTTCG CAGAAATCAC   720
```

Fig. 9B

```
TATCAATTTG GGATGTGATC AGCGCTTCAA GCCTCGAGAC GGATGCTCAA GTAGTGCTGA    780
CACCGGCTTG CGTGGCGGTA TAATCAATCA GAATTCTCCA TGAATAAGGA GAAGCTTGGG    840
GTTTGAAGCC TCGATGAAGA AGCTTGACTC CGGTCACTCC ACTGAGCTTC TGAGCGAAAG    900
CAGTAGAGAT CATCATCGAA AGGGGTTCTG ACACTTAATG TCACAAGGCA GGAAGCCACA    960
ATCAACATCC GACAGGACGG AGAATCTTCA GCCTGCTTGA GTCTCAGCGC CTGGCGGGGG   1020
TGGAGGATGA GTATACGTTG TAGATTCTCC GGTGGACATG AGCCCTTGAC CATAATCACC   1080
ATGAAGGCTC CTTACTGCGA TATAAAAGCT GCAGTTTCTG CGTAGGTTCT TGAGGAGAAT   1140
CCCAAGAATC AAGCAAATCG AGGTTGCTCC CATTGATTCA AGTGAATC ATG CGT GCT   1197
                                                    Met Arg Ala
                                                        -18

CTT TTC CTT CTT GCG CTC GGT TCT ATC CCG GCG CTC GTC AGC GGT CAA    1245
Leu Phe Leu Leu Ala Leu Gly Ser Ile Pro Ala Leu Val Ser Gly Gln
 -15                 -10                  -5                   1
```

Fig. 9C

```
CTC TCT GGC AGT GTT GGC CCC TTG ACC TCT GCT TCC ACC AAA GGT GCG    1293
Leu Ser Gly Ser Val Gly Pro Leu Thr Ser Ala Ser Thr Lys Gly Ala
              5                  10                  15

ACA AAA ACA TGC AAT ATC CTC AGC TAC GGC GCA GTG GCC GAC AAC TCG    1341
Thr Lys Thr Cys Asn Ile Leu Ser Tyr Gly Ala Val Ala Asp Asn Ser
             20                  25                  30

ACC GAT GTT GGG CCT GCC ATT ACA TCG GCC TGG GCT GCA TGC AAG AGC    1389
Thr Asp Val Gly Pro Ala Ile Thr Ser Ala Trp Ala Ala Cys Lys Ser
             35                  40                  45

GGA GGT CTT GTC TAC ATC CCA TCT GGC AAC TAT GCC TTA AAC ACC TGG    1437
Gly Gly Leu Val Tyr Ile Pro Ser Gly Asn Tyr Ala Leu Asn Thr Trp
             50                  55                  60

GTC ACC CTG ACT GGA GGC AGT GCG ACC GCA ATC CAG CTG GAT GGT ATC    1485
Val Thr Leu Thr Gly Gly Ser Ala Thr Ala Ile Gln Leu Asp Gly Ile
             70                  75                  80
```

Fig. 9D

```
ATT TAT CGC ACA GGT ACC GCC AGT GGG AAC ATG ATT GCA GTC ACT GAC       1533
Ile Tyr Arg Thr Gly Thr Ala Ser Gly Asn Met Ile Ala Val Thr Asp
 85                      90                      95

ACC ACC GAC TTC GAG CTG TTC AGT AGC ACC TCC AAA GGT GCT GTG CAG       1581
Thr Thr Asp Phe Glu Leu Phe Ser Ser Thr Ser Lys Gly Ala Val Gln
            100                     105                     110

GGA TTC GGC TAT GTG TAC CAT GCG GAG GGA ACC TAC GGA GCA CGG ATT       1629
Gly Phe Gly Tyr Val Tyr His Ala Glu Gly Thr Tyr Gly Ala Arg Ile
115                     120                     125

CTG CGC TTG ACT GAT GTG ACC CAT TTC TCT GTG CAT GAT GTG ATC TTG       1677
Leu Arg Leu Thr Asp Val Thr His Phe Ser Val His Asp Val Ile Leu
130                     135                     140                 145

GTG GAT GCG CCT GCT TTC CAC TTT ACC ATG GAT ACC TGC TCC GAT GGG       1725
Val Asp Ala Pro Ala Phe His Phe Thr Met Asp Thr Cys Ser Asp Gly
            150                     155                     160
```

Fig. 9E

```
GAG GTG TAC AAC ATG GCG ATT CGT GGT GGC AAT GAG GGC GGC TTG GAC           1773
Glu Val Tyr Asn Met Ala Ile Arg Gly Gly Asn Glu Gly Gly Leu Asp
                165                 170                 175

GGG ATT GAT GTC TGG GGA AGC AAC ATC TGG GTT CAC GAT GTAAGTCACG            1822
Gly Ile Asp Val Trp Gly Ser Asn Ile Trp Val His Asp
        180                 185                 190

CCCGAGTGGC AATATGCTAC TTCTCTGTCG CTCACGAGAT GTGCACTCAT TTAG GTT           1879
                                                            Val

GAA GTG ACC AAC AAG GAT GAA TGT GTA ACA GTC AAG GTAAGGCTTT                1925
Glu Val Thr Asn Lys Asp Glu Cys Val Thr Val Lys
            195                 200

CCCTTGCAAG CACGAATTGA CGGCGCTCGAG CCTTGATTGA CAGACGGACC GCAG AGC          1982
                                                              Ser
```

Fig.9F

```
CCG GCC AAC AAT ATT CTG GTG GAG AGC ATC TAT TGC AAC TGG AGT GGT    2030
Pro Ala Asn Asn Ile Leu Val Glu Ser Ile Tyr Cys Asn Trp Ser Gly
205                 210                 215                 220

GGT TGC GCA ATG GGG TCG CTC GGG GCC GAC ACC GAC GTC ACC GAT ATT    2078
Gly Cys Ala Met Gly Ser Leu Gly Ala Asp Thr Asp Val Thr Asp Ile
            225                 230                 235

GTC TAC CGC AAT GTT TAC ACC TGG TCA TCG AAC CAG ATG TAC ATG ATC    2126
Val Tyr Arg Asn Val Tyr Thr Trp Ser Ser Asn Gln Met Tyr Met Ile
        240                 245                 250

AAG AGC AAT GGC GGT AGT GGA ACG GTG TCG AAT GTT TTG CTG GAA AAT    2174
Lys Ser Asn Gly Gly Ser Gly Thr Val Ser Asn Val Leu Leu Glu Asn
    255                 260                 265

TTC ATC G GTCAGTGCTG CTGCCTATGC CCCCACCTTT CTGGCTTGAA ACTGTTAACT   2231
Phe Ile
270
```

Fig. 9G

```
GATCCCCTTT ATTTAG  GG CAC GGT AAT GCG TAC TCG CTC GAC ATC GAC      2279
                      Gly His Gly Asn Ala Tyr Ser Leu Asp Ile Asp
                                          275                 280

GGC TAC TGG AGC AGC ATG ACT GCG GTG GCC GGG GAC GGG GTG CAG CTG    2327
Gly Tyr Trp Ser Ser Met Thr Ala Val Ala Gly Asp Gly Val Gln Leu
                285                             290             295

AAC AAC ATC ACG GTG AAG AAC TGG AAG AAC ACC GAG GCG AAC GGA GCG    2375
Asn Asn Ile Thr Val Lys Asn Trp Lys Asn Thr Glu Ala Asn Gly Ala
            300                             305                 310

ACC CGA CCA CCG ATC CGA GTG TGT AGT GAC ACG GCG CCT TGC ACG        2423
Thr Arg Pro Pro Ile Arg Val Val Cys Ser Asp Thr Ala Pro Cys Thr
315                             320                             325

GAC TTG ACG CTG GAA GAC ATT GCC ATC TGG ACC GAA AGC GGC TCG AGT    2471
Asp Leu Thr Leu Glu Asp Ile Ala Ile Trp Thr Glu Ser Gly Ser Ser
                330                             335             345
                                                        340
```

Fig. 9H

```
GAA CTG TAC CTG TGC CGT TCC GCT TAC GGA TCG GGA TAC TGT TTG AAG    2519
Glu Leu Tyr Leu Cys Arg Ser Ala Tyr Gly Ser Gly Tyr Cys Leu Lys
                350                     355                 360

GAC AGC TCT TCG CAC ACA TCC TAC ACC ACA ACC AGC ACT GTC ACG GCG    2567
Asp Ser Ser Ser His Thr Ser Tyr Thr Thr Thr Ser Thr Val Thr Ala
                365                     370                 375

GCT CCC TCA GGA TAT TCG GCG ACA ACC ATG GCA GCC GAC TTG GCA ACC    2615
Ala Pro Ser Gly Tyr Ser Ala Thr Thr Met Ala Ala Asp Leu Ala Thr
                380                     385                 390

GCA TTT GGT CTC ACT GCT TCC ATT CCC ATT CCG ACC ATC CCG ACC TCG    2663
Ala Phe Gly Leu Thr Ala Ser Ile Pro Ile Pro Thr Ile Pro Thr Ser
                395                     400                 405

TTT TAT CCC GGG TTG ACC CCG TAC AGT GCC TTG GCA GGC TAGTAGGTGT     2712
Phe Tyr Pro Gly Leu Thr Pro Tyr Ser Ala Leu Ala Gly
410                     415                     420
```

Fig. 9I

```
GAAAGCAAGG TGGGATTGAT GTGTCACCGT CGCCAGTGGAA GGAATGTCGG GAGAAGGAGA       2772
AGGAGAAGGA GAAGGAGAAG GAGGAGAGAT CGTTGAATCG TTGAGTCGTT GAGTCGTTGA       2832
GATCATGGAT CAGGCTGGTA ATCGTTACCT CACGATTCCG TAGGTGTTTG TAAGTAAGTA       2892
TGTATGTTAT ATCAATCAAA AGGAAGATCC TCCTTCGTAT CTCGAGATTT CTTTCATGCA       2952
GGACTGGGAA GGAGGAAGTT TGAGGAGTTC ATGTGAGCTG CAGTCGTCAG TTTCTCAGTC       3012
ACTCATTGTC CGATCGCGCC ATCCCTTCCT GGTCACTTCT AGTGCGCTTC CTTGCCCTTT       3072
TTTTACCTTT CTCTCCCATC ATCGTTCTCT TTCTCTTTCT CTCACTCCTC TCGCAGGTTC       3132
TGACTCTTTG ATCCCATTGC AAATATACCA CCTGCATCTT TCTGGAAGCG ATTGAGGAGA       3192
TGGTGAAGTG ATCAAGTGGA GAAGAGGTGA AAGTGGAAGC TGCACCGAGA ATAAGCTT         3250
```

METHODS OF DETECTING AND ISOLATING A RIPENING FORM OF A POLYPEPTIDE HAVING RHAMNOGALACTURONASE ACTIVITY

This is a division of application Ser. No. 08/061,062, filed May 14, 1993.

The present invention relates to the field of recombinant DNA technology and more in particular relates to its use in view of the biotechnological production of a polypeptide having rhamnogalacturonase activity. A polypeptide having rhamnogalacturonase activity is a polypeptide that can partly degrade pectin molecules and can be used in any context where degradation of pectin molecules is desirable, such as in the processing of fruit and vegetables, in the extraction of food ingredients by degradation of plant cell walls or in brewing processes.

BACKGROUND OF THE INVENTION

During fruit juice manufacture enzyme preparations are often used in the steps of extraction and liquefaction of fruit and fruit juice clarification (Voragen 1989). The commercial enzyme preparations contain a mixture of mainly pectinases (e.g. polygalacturonases, pectin esterases, pectin transeliminases) together with minor quantities of other hydrolytic enzymes such as arabinases, galactanases and xylanases. The substrates for the various pectinases are pectins, which are polygalacturonides of high molecular weight (20000–40000 D) consisting of α-1,4-glycosidic bound D-galacturonic acid polymers. Some of the uronic acid groups are esterified with methanol. The polygalacturonic backbone is interrupted by so-called hairy regions, consisting of a rhamnose-galacturonic acid backbone with arabinose-rich side chains (Voragen and Beldman 1990).

Pectins occur in nature as constituents of higher plant cell walls. They are found in the primary cell wall and middle lamella where they are embedded in cellulose fibrils (Mc Neil et al. 1984). The composition of pectin and the degree of methylation is variable among plant species and moreover dependent on the age and maturity of the fruit. Among the richest sources of pectins are lemon and orange rind, which can contain up to 30% of this polysaccharide.

Pectinases can degrade the carbohydrate polymer either by hydrolysis of the α-1,4-glycosidic bond (endo and exopolygalacturonases or by transelimination reaction (pectin lyases). Pectin esterases can demethylate highly esterified pectin into polygalacturonic acid. Pectin lyases are specific for highly esterified pectins, polygalacturonases hydrolyse low esterified pectins. Consequently highly esterified pectins can be degraded by pectin lyases or the combination of pectin esterases and polygalacturonases (Pilnik 1982).

In the various stages of fruit and vegetable processing pectinases play an important role. Originally pectinases were used for treatment of soft fruit to ensure high yields of juice and pigments upon pressing and to clarify raw press juices. Polygalacturonases are used as macerating enzymes for the production of pulpy nectars, loose cell suspensions that are the result of limited pectin breakdown particularly in the middle lamella. A combination of several pectinases together with cellulolytic enzymes is needed to almost completely liquefy fruit tissue, thereby facilitating extraction (Renard et al. 1989). The clarification of apple juices can for example be improved by the combined activity of pectin esterases and polygalacturonases or by pectin lyases for which the highly esterified apple pectin is an ideal substrate (Ishii and Yokotsuka 1973).

Most of the pectinases present in commercial preparations are of fungal origin. *Aspergillus niger* is the most important organism for the industrial production of pectin degrading enzymes. In *A. niger* the various pectinases are not expressed constitutively (Maldonado et al. 1989). Pectin or degradation products of the pectin molecule are needed as inducing substances. The fermentation conditions for pectinase production often result in a wide spectrum of pectinases. Moreover, *A. niger* produces many isoenzymes of the various pectinases. Recently patents have been published describing that genes encoding polygalacturonase (EPO 0421 919, EPO 0 388 593), pectin lyases (EPO 0 278 355, EPO 0 353 188) and pectin esterases (EPO 0 388 593) have been isolated and used for the construction of overproducing transformants. These transformants allow the production of specific enzymes, needed e.g. in maceration applications and in studies on the effect of the various pectinases in processes like liquefaction and clarification.

Schols et al. (*1990*b) have described the isolation and characterization of a cell-wall polysaccharide from apple juice obtained after the liquefaction process in which the juice was released from the apple pulp by the combined action of pectolytic and cellulolytic enzymes. These cell-wall polysaccharides resemble the hairy regions of apple pectin (a rhamnose-galacturonic acid backbone with arabinose rich side chains) and have been called Modified Hairy Regions (MHR). Hairy regions are known to be present not only in apples but also in carrots, grapes and strawberries and are probably a common part of pectin molecules. The modified hairy regions are resistant to breakdown by the enzymes present in most pure and technical pectinase and cellulase preparations. So only a commercial crude enzyme preparation obtained from *Aspergillus aculeatus* has been found to be able to depolymerize the rhamnogalacturon backbone of these fragments. This activity was made visible by measuring the shift in molecular weight distribution using High Performance Gel Permeation Chromatography (HPGPC). Schols et al. (*1990*a) purified the enzyme responsible for the degradation of the modified hairy regions prepared from apple juice and called the enzyme rhamnogalacturonase (RGase). The enzyme can split glycosidic linkages in the rhamnogalacturonan backbone of (apple) pectins producing, besides other not yet fully identified reaction products, a range of oligomers composed of galacturonic acid, rhamnose and galactose with rhamnose at the non reducing end, hence the name rhamnogalacturonase (RG-ase) for this novel enzyme. The oligomers present after incubation of MHR with rhamnogalacturonase were found to be a mixture of a tetramet (Rhamnose(2)-Galacturonic acid(2)) and a hexamer (Rhamnose(2)-Galacturonic acid(2)-Galactose(2) (Colquhoun 1990)). Schols et al (1990a) used various chromatographic steps and column materials to isolate and purify the enzyme with RG-ase activity. Rhamnogalacturonase was found to be inactive against MHR but was very active towards MHR-S and MHR-HCl. MHR-S is saponified MHR in which the methoxycarbonyl and acetyl groups have been removed. MHR-HCl is MHR from which the arabinan groups have been removed. Rhamnogalacturonase further exhibited no degrading activity against a polysaccharide fraction (SPS) present in soy-bean isolates in contrast to the commercial enzyme preparation itself which is known to possess activity against SPS (UK Patent 2 115 820). This finding illustrates that the commercial enzyme preparation used is indeed a crude enzyme preparation comprising various enzymes with different activities. In their paper Schols et al (1990a) suggest that rhamnogalacturonase may be useful in studies of the structures of complex pectic polysaccharides, but no further applications are suggested.

No commercial preparations of pure rhamnogalacturonase or comprising a defined and regulated amount of rhamnogalacturonase are presently available. The only method for obtaining an enzyme with RG-ase activity described sofar is the isolation of the enzyme from the aforementioned commercial preparation according to Schols et al. 1990a, a method that is lengthy, requires a large number of steps and is uneconomical.

The object of the present invention therefore is to provide rhamnogalacturonase in a process that is economical and can lead to easy production of pure forms of the desired enzyme. Furthermore the invention is directed at novel polypeptides having RG-ase activity and at novel compositions comprising rhamnogalacturonase in a predetermined amount preferably in an amount greater than 0.01 weight % based on the total weight of polypeptides present in said composition, with more preference for an amount greater than 0.1%. The composition can comprise the polypeptide having rhamnogalacturonase activity alone or in combination with other (hemi)cellulolytic enzymes or pectinases.

SUMMARY OF THE INVENTION

The present invention is directed at providing recombinant DNA material comprising DNA with at least a nucleotide sequence encoding a ripening form of a polypeptide having rhamnogalacturonase activity.

It is also an object of the present invention to provide a cell capable of expression, preferably capable of overexpression of a ripening form of a polypeptide having rhamnogalacturonase activity encoded by recombinant DNA material.

The recombinant DNA material comprising a nucleotide sequence encoding a ripening form of a polypeptide having rhamnogalacturonase activity can comprise a nucleotide sequence derivable from an organism that is homologous to the expression host cell into which cell said nucleotide sequence is incorporated or said nucleotide sequence can be heterologous to the expression host cell.

The expression of the nucleotide sequence encoding a ripening form of a polypeptide having rhamnogalacturonase activity can be regulated by operably linking said nucleotide sequence to regulatory sequences that control a gene native to the organism from which said nucleotide sequence has been derived. The regulatory sequences can also be foreign i.e. derived from an organism belonging to a different strain, variety, genus or group of organisms than the organism from which the nucleotide sequence encoding a polypeptide with rhamnogalacturonase activity has been derived. The regulatory regions can be regulatory regions of a rhamnogalacturonase gene or regulatory regions of other genes.

Another preferred embodiment of the invention is a cell capable of overexpression and secretion of a ripening form of a polypeptide having rhamnogalacturonase activity, preferably a mature form.

It is yet a further object of the present invention to provide a method for the production of a ripening form of a polypeptide having rhamnogalacturonase activity which may in turn advantageously be used in processes requiring degradation and/or modification of pectin, in particular at processes requiring degradation and/or modification of plant cell wall material. In particular the invention is directed at a process for improved liquefaction of fruit and/or vegetables and at a process for preventing and/or removing haze formation in particular the haze arising after dilution of concentrates derived from fruit and/or vegetables. The invention is also directed at rhamnogalacturonase comprising products suitable for use in such processes.

DETAILED DESCRIPTION OF THE INVENTION

Figure 1A:
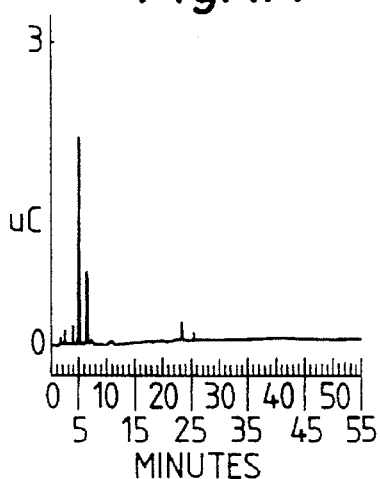
Figure 1B:
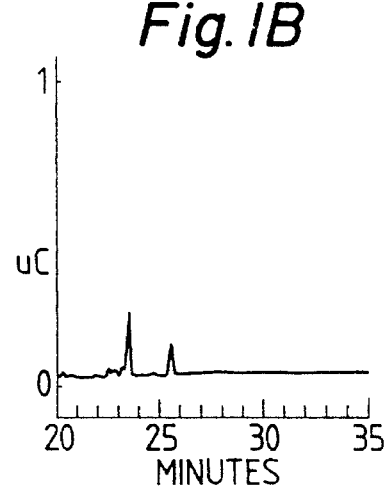
Figure 1C:
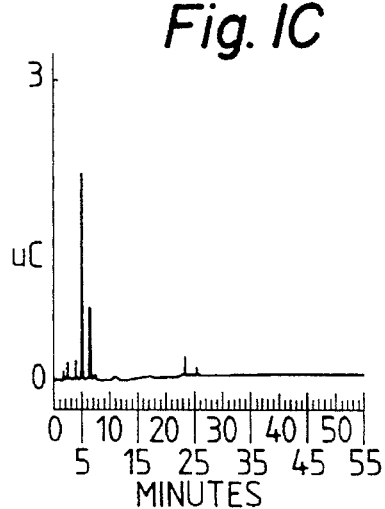
Figure 1D:
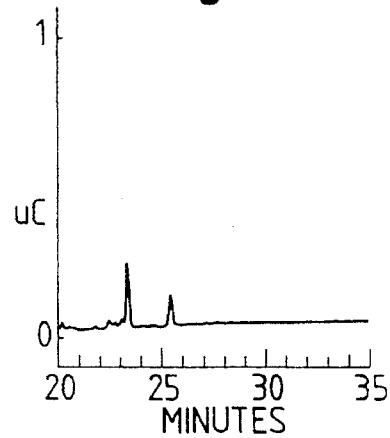
Figure 1E:
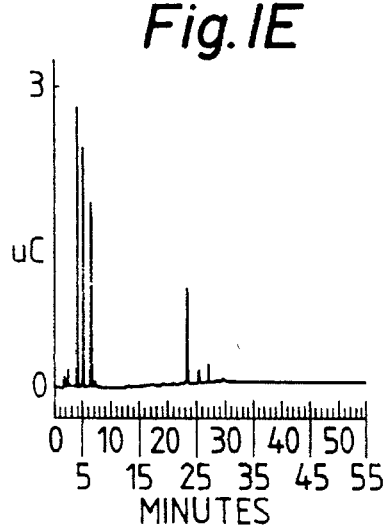
Figure 1F:
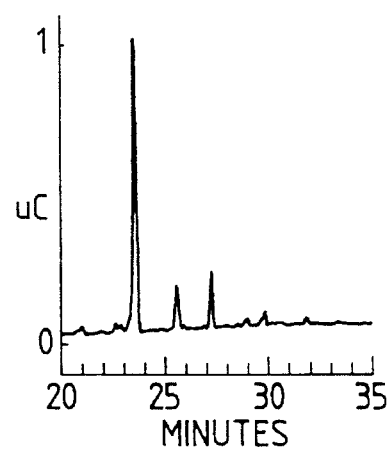

The present invention is directed at a recombinant DNA material comprising a DNA sequence encoding a ripening form of a polypeptide having rhamnogalacturonase activity or a precursor of said polypeptide or which recombinant DNA material is capable of producing a ripening form of a polypeptide having rhamnogalacturonase activity, comprising at least a part of a nucleotide sequence selected from the group consisting of a) a nucleotide sequence encoding a ripening form of a polypeptide having rhamnogalacturonase activity;

b) a genetic variant of a nucleotide sequence according to a);

c) a nucleotide sequence capable of hybridizing to either of the nucleotide sequences a) or b).

The term "recombinant DNA material" can comprise a DNA molecule, or a mixture of various DNA fragments/molecules.

The term "genetic variant" as used herein includes hybrid DNA sequences comprising at least a part of a nucleotide sequence encoding a ripening form of a polypeptide having rhamnogalacturonase activity optionally coupled to regulatory regions such as promoter, secretion and terminator signals originating from homologous or heterologous organisms. The term "genetic variant" also includes DNA sequences encoding mutant rhamnogalacturonase polypeptides, i.e. polypeptides comprising mutations not affecting the RG-ase activity and degenerate DNA sequences encoding polypeptides wherein the rhamnogalacturonase activity is retained. The term "genetic variant" also includes synthetic DNA sequences encoding polypeptides having rhamnogalacturonase activity.

The present invention also includes recombinant DNA material comprising at least a part of a nucleotide sequence capable of hybridizing to at least a part of the nucleotide sequence encoding a ripening form of a polypeptide having rhamnogalacturonase activity and genetic variants thereof as described above which may differ in codon sequence due to the degeneracy of the genetic code or cross species variation. For hybridisation to occur homology between the DNA material must be higher than 40%. Preferably the homology is larger than 70%. The hybridisation conditions can be adjusted to correspond to conditions required for the desired degree of homology. The more stringent the hybridisation conditions, the more homology hybridising sequences will show. A person skilled in the art can carry out such hybridisation tests.

The term "ripening form" refers to any of the different forms in which an enzyme may occur after expression of the associated gene. More in particular it refers to both the naturally and not naturally occurring mature form of an enzyme that can result after cleavage of a "leader" peptide and also to any form of an enzyme still comprising a "leader" peptide in any form. In general a "leader peptide" can be a prepro peptide, a pre peptide or a pro peptide.

The recombinant DNA material according to the invention can comprise at least a part of a nucleotide sequence encoding a ripening form of a polypeptide having rhamnogalacturonase activity wherein said nucleotide sequence can be derived from any organism varying from a mammal to a microorganism.

With a view to application in processes directed at the production of foodstuffs, a preferred recombinant DNA material according to the invention will comprise a nucleotide sequence encoding a ripening form of a polypeptide having rhamnogalacturonase activity originating from a foodgrade organism.

As already stated the nucleotide sequence encoding a ripening form of a polypeptide having rhamnogalacturonase activity can be of microbial origin. Such a sequence can be derived from a microorganism such as a fungus preferably a foodgrade fungus. Suitable fungi are the filamentous fungi e.g. the group comprising the genera *Aspergillus, Trichoderma, Neurospora, Penicillium* and *Mucor*. Of the genus *Aspergillus* the species of the group comprising *Aspergillus niger, Aspergillus awamori, Aspergillus oryzae, Aspergillus sojae, Aspergillus foetidus, Aspergillus carbonarius, Aspergillus tubigensis, Aspergillus aculeatus* and *Aspergillus japonicus* are eminently suitable examples of organisms from which a nucleotide sequence encoding a ripening form of a polypeptide having rhamnogalacturonase activity can be derived.

A more concrete preferred embodiment of this aspect of the invention is recombinant DNA material comprising at least a part of a nucleotide sequence encoding a ripening form of a polypeptide having rhamnogalacturonase activity with the amino acid sequence shown in FIG. 9, (sequence listing no. 7) and even more concretely a recombinant DNA material comprising at least a part of the nucleotide sequence as shown in FIG. 9A–9I (sequence listing no. 7). The genetic variants of the nucleotide sequence of FIG. 9A–9I (sequence listing no. 7) including sequences encoding mutant rhamnogalacturonase polypeptides and degenerate nucleotide sequences coding for polypeptides wherein the rhamnogalacturonase activity is retained are also part of the invention, as are nucleotide sequences capable of hybridizing to at least a part of the nucleotide sequences encoding a polypeptide having rhamnogalacturonase activity as shown in FIG. 9A–9I (sequence listing no. 7) and genetic variants thereof (as described above), wherein said nucleotide sequences may differ in codon sequence due to the degeneracy of the genetic code or cross species variation.

A polypeptide having rhamnogalacturonase activity derived from *Aspergillus aculeatus* was used to obtain the nucleotide sequence and amino acid sequence given in figure 9A–9I (sequence listing no. 7). Based on the cross-reaction observed between antibody raised against rhamnogalacturonase of *Aspergillus aculeatus* and enzymes of other microorganisms it is clear that various other organisms comprise a polypeptide with rhamnogalacturonase activity.

Rhamnogalacturonase activity has now been found in a number of strains and derivatives of the genus Aspergillus besides the *Aspergillus aculeatus* strain used for preparing the commercial preparation (CBS 101.43), e.g. *Aspergillus niger* 402 (CBS 120.49), *Aspergillus niger hennebergii* (CBS 117.80), *Aspergillus carbonarius* (CBS 112.80, CBS 420.64), *Aspergillus niger nanus* (CBS 136.52, CBS 117.48), *Aspergillus foetidus* (CBS 121.78, CBS 618.78), *Aspergillus tubigensis* (CBS 11529), *Aspergillus niger intermedius* (CBS 559.65) and *Aspergillus japonicus* (CBS 114.51, CBS 621.78), *Aspergillus aculeatus* (CBS 115.80, CBS 172.66, CBS 119.49).

The subject invention is therefore directed at polypeptides with rhamnogalacturonase activity derivable from these microorganisms. Furthermore the invention is also directed at antibodies raised against any such polypeptides with rhamnogalacturonase activity. The invention is directed at both antibodies with specificity in general for rhamnogalacturonase but also at antibodies specific for one specific type of rhamnogalacturonase. As illustrated in Example I, a person skilled in the art can arrive at such antibodies in a manner well known in the art.

The invention is also directed at use of such antibodies capable of recognizing at least one antigenic determinant of a polypeptide with rhamnogalacturonase activity for detecting and/or selecting a polypeptide or a cell having rhamnogalacturonase activity in a manner well known to a person skilled in the art.

Using hybridisation techniques a part of the isolated DNA encoding a polypeptide having rhamnogalacturonase activity can also be used to screen other organisms for a DNA sequence having homology with said isolated DNA. The hybridizing part of the genetic material of the other organism can be assumed to comprise at least a part of a nucleotide sequence encoding a ripening form of a polypeptide having rhamnogalacturonase activity. Using the process for recovering such a nucleotide sequence as given in Example I, a person skilled in the art can derive a nucleotide sequence encoding a ripening form of a polypeptide having rhamnogalacturonase activity from another organism. Use of stringent hybridisation conditions enables selection of antibodies that bind very strongly to the polypeptide. A person skilled in the art knows what hybridisation conditions to select.

The recombinant DNA material according to the invention can be used to express a nucleotide sequence encoding a ripening form of a polypeptide having rhamnogalacturonase activity or the recombinant DNA material can be used as a probe or a primer for detection, isolation or production of genetic material encoding at least a part of a ripening form of a polypeptide with rhamnogalacturonase activity or a precursor of such ripening form.

The recombinant DNA material according to the invention can comprise the nucleotide sequence encoding a ripening form of a polypeptide having rhamnogalacturonase activity operably linked to at least one regulatory region capable of directing the expression of said nucleotide sequence. The regulatory regions can be native to the organism from which the nucleotide sequence encoding the polypeptide having rhamnogalacturonase activity is derived. Said native regulatory regions can be the regulatory regions that regulate the rhamnogalacturonase gene in the organism of origin of said polypeptide but can also be regulatory regions that regulate a different gene in said organism of origin. A regulatory region other than the native regulatory region that regulates the rhamnogalacturonase gene in the organism of origin of said gene will generally be selected for its higher efficiency. It is also possible to select a regulatory region such as a promoter on the basis of other desirable characteristics, for example thermo inducibility. The selection of a desirable regulatory region will be obvious to one skilled in the art.

In another embodiment the recombinant DNA material according to the invention can comprise regulatory regions foreign to the organism from which the nucleotide sequence encoding the polypeptide having rhamnogalacturonase activity is derived operably linked to said nucleotide sequence. In this instance the regulatory regions can be regulatory regions that regulate a rhamnogalacturonase gene in the foreign organism from which they are derived or can be regulatory regions that regulate a gene other than the rhamnogalacturonase gene in the foreign organism.

The selection of a desirable regulatory region will be obvious to one skilled in the art and will for example depend on the host cell into which the recombinant DNA material according to the invention is introduced. If a heterologous expression host is preferred, meaning that the nucleotide sequence encoding a polypeptide having rhamnogalacturonase activity is derived from another strain of organism than the host cell (e.g. a different strain, variety, species, genus, family, order, class, division or kingdom) the regulatory region is preferably a regulatory region derived from an organism similar to or equal to the expression host. For example, if the nucleotide sequence is derived from a fungus and the expression host is a yeast cell, then the regulatory region will be derived from a yeast cell. The regulatory region need not however necessarily be derived from the same strain or the same genus as the host cell, i.c. a yeast cell. The selection of a yeast cell promoter in this instance is required to enable expression of the nucleotide sequence.

A regulatory region operably linked to a nucleotide sequence encoding a ripening form of a polypeptide having rhamnogalacturonase activity in the recombinant DNA material according to the invention can be e.g. a constitutive promoter or an inducible promoter. Especially suited are constitutive promoters derived from genes encoding enzymes involved in the glycolytic pathway.

An example of a recombinant DNA material according to the invention comprising a strong constitutive fungal promoter operably linked to the nucleotide sequence encoding a ripening form of rhamnogalacturonase activity is a recombinant DNA material wherein said promoter is the glyceraldehyde-3-phosphate dehydrogenase (gpdA) promoter. This promoter is preferred for constitutive expression when recombinant DNA material according to the invention is expressed in a fungal expression host. Other examples are pgk, the phosphoglycerate kinase promoter, pki, the pyruvate kinase promoter, TPI, the triose phosphate isomerase promoter, the APC synthetase subunit g (oliC) promoter and the acetamidase (amdS) promoter.

Examples of recombinant DNA material according to the invention comprising inducible fungal promoters operably linked to the nucleotide sequence encoding a ripening form of rhamnogalacturonase activity are recombinant DNA materials, wherein said inducible promoters are selected from the promoters of the following genes: xylanase A (xylA), glucoamylase A (glaA), cellobiohydrolase (cbh), amylase (amy), invertase (suc) and alcohol dehydrogenase alcA, TAKA amylase and amyloglucosidase (AGT). Preferably the inducible xylanase A promoter is selected.

Examples of recombinant DNA material according to the invention comprising strong yeast promoters operably linked to the nucleotide sequence encoding a ripening form of rhamnogalacturonase activity are recombinant DNA materials, wherein said yeast promoters are selected from the promoters of the following genes: alcohol dehydrogenase, lactase, 3-phosphoglycerate kinase, triose phosphate isomerase, α-D-galactose-phosphate uridyl transferase (Gal7) and glyceraldehyde-3-phosphate dehydrogenase (GAPDH).

Examples of recombinant DNA material according to the invention comprising bacterial promoters operably linked to the nucleotide sequence encoding a ripening form of rhamnogalacturonase activity are recombinant DNA materials, wherein said bacterial promoters are selected from the promoters of the following genes: α-amylase, SPO2 and extracellular proteases.

In the same manner that regulating regions foreign to the rhamnogalacturonase gene can be coupled to said gene, it is also possible to couple a regulating region of a rhamnogalacturonase gene to a heterologous gene. The invention is therefore also directed at a nucleotide sequence comprising at least a regulating region of a rhamnogalacturonase gene e.g. as indicated in FIG. 9A–9I (sequence listing no. 7) and at use of such a nucleotide sequence e.g. for regulating the expression of the gene to which said sequence is coupled.

If a heterologous expression host is a yeast or a bacterial strain a recombinant DNA material according to the invention comprising an uninterrupted (intronless) nucleotide sequence encoding a ripening form of a polypeptide having rhamnogalacturonase activity is preferred. This preference stems from the fact-that the possibility that the heterologous host does not recognize splicing signals residing on the recombinant DNA material can thus be avoided. Such an uninterrupted nucleotide sequence was obtained from a cDNA library constructed from RNA isolated from cells expressing a nucleotide sequence encoding a ripening form of a polypeptide with rhamnogalacturonase activity and is presented in FIG. 6A–6F, sequence listing no. 5). Alternatively an uninterrupted nucleotide sequence may be obtained by applying one or more polymerase chain reactions using suitable primers, so as to precisely remove the introns, using genomic DNA as a template, as is known to a person skilled in the art.

For the expression in yeast such as *Saccharomyces cerevisiae* it is preferable that the introns are removed and that the fungal rhamnogalacturonase leader sequence is replaced by a signal sequence suitable for yeast such as the signal sequence of the invertase gene ensuring correct processing and secretion of the mature polypeptide.

The removal of introns is necessary for expression in bacteria such as *Bacillus subtilis*. In this case for example the α-amylase signal sequence can be used as signal sequence.

A preferred embodiment of recombinant DNA material according to the invention comprises at least one selection marker. Such a selection marker serves to discriminate host cells into which the recombinant DNA material has been introduced from cells that do not comprise said recombinant DNA material. This selection marker provided with the appropriate regulatory sequences may reside on the same DNA fragment containing the nucleotide sequence encoding a ripening form of a polypeptide having rhamnogalacturonase activity or can be present on a separate fragment. In the latter case a co-transformation must be performed with the various components of the recombinant DNA material according to the invention. The ratio of expression component (containing the nucleotide sequence encoding a ripening form of a polypeptide having rhamnogalacturonase activity)/selection component (with the selection marker) can be adjusted in such a manner that a high percentage of the selected cells comprising the selection component have also incorporated the expression component. The term recombinant DNA material as used herein therefore comprises one or more recombinant DNA fragments, wherein the selection marker can be incorporated on the same recombinant DNA molecule as the nucleotide sequence encoding a ripening form of a polypeptide having rhamnogalacturonase activity or on a different recombinant DNA fragment.

Very often filamentous fungi are transformed through co-transformation. For example a pyrA⁻ strain (pyrA=orotidine-5'-phosphate decarboxylase) can be used as host cell and the recombinant DNA material according to the invention will comprise a DNA molecule comprising the nucleotide sequence encoding a ripening form of a polypeptide having rhamnogalacturonase activity and another DNA molecule comprising the pyrA gene. After transformation of the pyrA⁻ strain any resulting pyrA⁺ strain will obviously have incorporated some recombinant DNA material and will most probably also comprise the nucleotide sequence encoding a ripening form of a polypeptide having rhamnogalacturonase activity. Very often such co-transformation will lead to incorporation of the component of recombinant DNA material according to the invention comprising the nucleotide sequence encoding a ripening form of a polypeptide having rhamnogalacturonase activity per host cell in multiple copies (multicopy incorporation). This is a well-known route for producing multicopy tranformants in general.

Other well-known selection systems for industrial microorganisms are those formed by the group of selection markers which do not require a mutation in the host organism. Examples of fungal selection markers are the genes for acetamidase (amdS), ATP-synthetase, subunit 9 (oliC) and benomyl resistance (benA). Another example of a fungal selection marker is the nitrate reductase system. Exemplary of non-fungal selection markers are the g418 resistance gene (yeast), the ampicillin resistance gene (*E. coli*) and the neomycin resistance gene (Bacillus), a gene conferring resistance to hygromycin (hph) or a gene conferring resistance to fleomycin (Ble).

Suitable transformation methods and suitable expression vectors provided with e.g. a suitable transcription promoter, suitable transcription termination signals and suitable marker genes for selecting transformed cells are already known for many organisms including different bacterial, yeast, fungal and plant species. Reference may be made for yeast for example to Tagima et al. Yeast 1, 67–77, 1985, which shows expression of a foreign gene under control of the gal7 promoter inducible by galactose in yeast and for *Bacillus subtilis* for example in EP-A-0,157,441 describing a plasmid pNS48 containing the SPO2 promoter as an expression vector. For the possibilities in these and other organisms reference is made to the general literature.

Overexpression of a ripening form of a polypeptide having rhamnogalacturonase activity may be achieved by the incorporation of recombinant DNA material according to the invention in an expression host, said recombinant DNA material comprising one or more regulatory regions (selected for example from promoter and terminator regions) which serve to increase expression levels of the polypeptide of interest from said expression host. If desired the polypeptide of interest can be secreted from the expression host. This can be achieved by incorporating recombinant DNA material according to the invention as described, said DNA material further comprising at least one signal sequence (e.g. a pre or prepro sequence).

The present invention is not only directed at the recombinant DNA material comprising at least a part of a nucleotide sequence encoding a ripening form of a polypeptide having rhamnogalacturonase activity in the various embodiments as described above but is also directed at a cell comprising at least a part of such recombinant DNA material, said cell being capable of expression of said nucleotide sequence.

Progeny of an expression host comprising recombinant DNA material according to the invention is also embraced by the present invention.

Preferably a cell according to the invention will be capable of overexpression of a nucleotide sequence encoding a ripening form of a polypeptide having rhamnogalacturonase activity. Within the context of the present invention overexpression is defined as the expression of the ripening form of a polypeptide having rhamnogalacturonase activity at levels above those ordinarily encountered under the same conditions in the native organism from which said polypeptide originates. In the same context overexpression also covers the expression of the ripening form of a polypeptide having rhamnogalacturonase activity in an organism other than the organism from which the nucleotide sequence comprised on the recombinant DNA material according to the invention can be derived, a so called heterologous organism. The heterologous host organism does not normally produce such a ripening form of a polypeptide having rhamnogalacturonase activity at appreciable levels and the heterologous organism is therefore only capable of such production after introduction of the recombinant DNA material according to the invention.

As already stated, overexpression of a ripening form of a polypeptide having rhamnogalacturonase activity may be achieved by incorporation of recombinant DNA material according to the invention.

In order to obtain overexpression recombinant DNA material according to the invention can be incorporated in a homologous expression host. The term "homologous expression host" means that the non transformed expression host belongs to the same strain or species as the organism from which the nucleotide sequence encoding a ripening form of a polypeptide having rhamnogalacturonase activity that is comprised on the recombinant DNA material according to the invention has been derived.

Introduction of the recombinant DNA material according to the invention into a homologous expression host will result in the expression host comprising at least two nucleotide sequences encoding a ripening form of polypeptide having rhamnogalacturonase activity, becoming a so-called multicopy transformant.

The overexpression can be further achieved by the introduction of the recombinant DNA material according to the invention into a host belonging to a strain other than the strain from which the nucleotide sequence encoding a ripening form of polypeptide having rhamnogalacturonase activity was isolated a so-called heterologous host, such that the resulting expression host comprises a nucleotide sequence encoding a ripening form of polypeptide having rhamnogalacturonase activity in increased gene copy numbers, becoming a so-called multicopy transformant.

The methods generally known for obtaining multicopy transformants can be used. The recombinant DNA material according to the invention therefore comprises any embodiment required for obtaining a multicopy transformant comprising multiple copies of the nucleotide sequence encoding a ripening form of polypeptide having rhamnogalacturonase activity.

The overexpression can also be achieved by the introduction of the recombinant DNA material according to the invention in the various embodiments already described into a host cell such that the host cell comprises the nucleotide sequence encoding a ripening form of polypeptide having rhamnogalacturonase activity under the control of a regulatory region other than the native regulatory region for the rhamnogalacturonase gene in the organism from which said nucleotide sequence is derived, said other regulatory region preferably being more efficient than the native regulatory region. The invention is also directed at recombinant DNA material in any of the various embodiments described further comprising a regulatory region other than the native regulatory region for the rhamnogalacturonase gene in the organism from which said nucleotide sequence is derived. Such a host cell can be either homologous or heterologous. The host cell can comprise one or more copies of the nucleotide sequence encoding a ripening form of polypeptide having rhamnogalacturonase activity comprised on the recombinant DNA material according to the invention.

In some instances it can be preferable to introduce recombinant DNA material according to the invention in such a manner that said recombinant DNA material is integrated in the chromosomal DNA of the host cell. In fungal cells chromosomal integration always takes place in successful transformations. No plasmid DNA is maintained. In yeast both plasmids and integrated DNA can be maintained satisfactorily.

It is possible to introduce recombinant DNA material into the host cell such that the genetic properties that are introduced are located on extra-chromosomal DNA most often called "plasmids". Plasmids have the advantage that they exist normally in the cell in multiple copies which also means that a certain gene located on such a plasmid exists in the cell in multicopy form which may result in a higher expression of the proteins encoded by the genes. However, the disadvantage of plasmids is that they can be unstable resulting in a possible loss of the plasmids from the cells at a certain stage. The loss of a plasmid can be prevented by using a plasmid comprising at least one stretch of nucleotides capable of hybridizing with chromosomal DNA of the non-transformed host cell enabling said vector to integrate stably into the chromosome of said host cell after transformation. Use of a stretch of homologous DNA that is already present in multiple copies in the chromosomal DNA will lead to multicopy insertion of the vector DNA resulting in integrated multimeric DNA comprising one or more copies of the nucleotide sequence encoding a ripening form of a polypeptide having rhamnogalacturonase activity. Another prerequisite for a vector resulting in DNA integrated in the chromosomal DNA is that the vector does not comprise a functional replicon as the vector must be unable to maintain itself in the host cell unless it is integrated.

The stretch of nucleotides enabling integration is preferably derivable from DNA that comprises at least part of a non-essential portion of the chromosome of a non-transformed host cell (in this instance the term "derivable from" implies that the stretch of nucleotides in the vector according to the invention must show enough homology with the chromosomal DNA to enable hybridization for an integration event to occur). The integration of the vector will subsequently take place in said non-essential portion of the chromosome of the host cell and will not lead to the loss of an essential function of the host cell. It is preferable for the integration to take place in a non-essential selectable gene of the chromosome of the non-transformed host cell. This can subsequently be a selection criterium for transformed host cells.

In the case of fungal cells it is only possible to successfully obtain transformants having DNA integrated in the chromosomal fungal DNA as plasmids cannot be maintained in such cells. In fungal cells it is not even necessary to include homologous chromosomal DNA as multicopy integration takes place without said homologous DNA. In the case of yeast cells it is optional to have the desired DNA in the transformant either as a plasmid or as integrated DNA. For integration in yeast cells DNA sequences homologous to chromosomal DNA must be present.

A preferred embodiment of the invention is directed at a cell comprising recombinant DNA material according to the invention in any of the embodiments described, wherein said cell is capable of secreting a ripening form in particular capable of secreting a mature form of a polypeptide with rhamnogalacturonan activity as encoded by said recombinant DNA material. It is often desirable for the ripening form of a polypeptide having rhamnogalacturonase activity to be secreted from the expression host into the culture medium as said polypeptide may be more easily recovered from the medium than from the cell. Preferably the mature form of the rhamnogalacturonase will be secreted into the culture medium.

The term "secretion" in the subject invention comprises the polypeptide crossing a cell wall or a cell membrane. The polypeptide can pass such a cell wall or membrane into the culture medium but can also remain attached to said cell wall or cell membrane. The polypeptide can also pass a cell membrane into the periplasmic space and not into the culture medium. The processing c.q. secretion route to be followed by the ripening form of a polypeptide having rhamnogalacturonase activity will depend on the selected host cell and the composition of the recombinant DNA material according to the invention. Most preferably, however, the polypeptide will be secreted into the culture medium.

The cell according to the invention can comprise recombinant DNA material in any of the various embodiments described further comprising DNA encoding the native leader sequence (pre or prepro) of the polypeptide having rhamnogalacturonase activity. In another embodiment the cell according to the invention can comprise recombinant DNA material further comprising DNA encoding for foreign leader sequences (pre or prepro) instead of the native leader sequences. The invention is also directed at recombinant DNA material comprising DNA encoding the mature polypeptide having rhamnogalacturonase activity coupled to DNA encoding a leader sequence foreign to the polypeptide having rhamnogalacturonase activity.

An increase in the expression of a polypeptide having rhamnogalacturonase activity can result in the production of polypeptide levels beyond those the expression host is capable of processing and secreting resulting in a build up of polypeptide product within the host cell creating a bottle neck in the transport of the polypeptide through the cell membrane or cell wall. Accordingly the present invention is also directed at a cell comprising recombinant DNA material in any of the various embodiments described comprising heterologous signal sequences to provide for the most efficient secretion of the rhamnogalacturonase from the chosen expression host and the invention is also directed at said recombinant DNA material.

A heterologous secretion signal sequence may be chosen such that it is derived from the same strain as the organism from which the other regulatory regions of the nucleotide sequence encoding a ripening form of a polypeptide having rhamnogalacturonase activity have been derived, preferably from the same gene. For example the signal of the highly secreted amyloglucosidase protein may be used in combination with the amyloglucosidase promoter itself as well as in combination with other promoters.

Examples of preferred heterologous secretion signal sequences are those originating from the glucoamylase A or xylanase A gene for fungi, the invertase gene for yeast and the α-amylase gene for Bacillus.

Hybrid secretion sequences may also advantageously be used within the context of the present invention.

In general terminators of transcription are not considered to be critical elements for the overexpression of genes. If desired, a terminator of transcription may be selected from the same gene as the promoter or alternatively the homologous terminator may be employed. In fact any terminator can be employed.

Factors such as size (molecular weight) the possible need for glycosylation or the desirability of the secretion over the cell membrane or cell wall or into the medium of the rhamnogalacturonase play an important role in the selection of the expression host.

Partly depending on the selected host cell the nucleotide sequence encoding a polypeptide having rhamnogalacturonase activity will be used either with or without introns occurring in said DNA sequence either with its own promoter and/or transcription termination signals or originating from another gene and either with its own leader sequence or with a signal sequence originating from another gene.

In principle the invention knows no special limitations with respect to the nature of the cells comprising recombinant DNA material according to the invention. Cells according to the invention may be important as agents for multiplying the recombinant DNA material or as agents for producing a ripening form of a polypeptide having rhamnogalacturonase activity.

Those expression hosts capable of overexpression of a nucleotide sequence encoding a ripening form of a polypeptide having rhamnogalacturonase activity are preferred. In particular an expression host cell capable of secretion of a ripening form of polypeptide having rhamnogalacturonase activity is preferred.

The expression hosts can be selected from the group consisting of bacterial cells, fungal cells, yeast cells and plant cells, with a preference for foodgrade host cells.

Preferred examples of eminently suited host cells are a) fungal cells, in particular filamentous fungal cells, such as a fungal cell from the group comprising the genera Aspergillus, Trichoderma, Neurospora, Penicillium and Mucor. Examples of particular species that are suitable as host cell are fungal cells of one of the species *Aspergillus niger, Aspergillus awamori, Aspergillus oryzae, Aspergillus nidulans, Aspergillus sojae, Aspergillus tubigensis, Aspergillus aculeatus, Aspergillus foetidus, Aspergillus carbonarius, Aspergillus japonicus, Trichoderma reesei* and *Trichoderma viride;* b) yeast cells, for example of the genera Saccharomyces, Kluyveromyces, Hansenula and Pichia, in particular yeast cells of one of the species *Saccharomyces cerevisiae, Saccharomyces carlbergensis, Kluyveromyces lactis, Kluyveromyces marxianus, Hansenula polymorpha* and *Pichia pastoris;* c) plant cells of a plant genus selected for example from the group consisting of wheat, barley, oats, maize, pea, potato, apple, grape, chicory, coffee, tea and tobacco such as plant cells of one of the species *Solanum tuberosum* and *Nicotiana tobaccum;* and d) bacterial cells, preferably gram positive bacterial cells, for example of one of the bacterial genera Bacillus, Lactobacillus and Streptococcus such as bacteria of the species *Bacillus subtilis* or *Bacillus licheniformis.*

The host cell to be selected for recombinant DNA material according to the invention will amongst others depend on the application for which the resulting polypeptide having rhamnogalacturonase activity is destined.

A preferred cell according to the invention is a foodgrade cell. This preference stems from the fact that products of such foodgrade cells can be used in processes for producing foodstuffs. Bacteria from the genus Bacillus are very suitable as expression host cells because of their capability to secrete proteins into the culture medium. Alternatively a host selected from the group of yeasts or fungi may be preferred. In some instances yeast cells are easier to manipulate than fungal cells. However, some proteins are either poorly secreted from the yeast cell or in some cases are not processed properly (e.g. hyperglycosylation in yeast). In these and other instances a fungal host organism can be selected. A fungal host is often suitable if it has GRAS status (GRAS=generally regarded as safe). In general, eukaryotic hosts have been found to have a high productivity of secreted active polypeptides. In fact fungal hosts are very often used in industrial processes, particularly suitable examples of a host cell are therefore *Aspergillus niger* and *Aspergillus niger var. awamori.* These particular species of Aspergillus have previously been demonstrated to be excellent host cells for industrially producing enzymes. A person skilled in the art is able to obtain multicopy transformants of these species.

In the case of polypeptide production it is possible to use the expression host cell to produce polypeptide and to subsequently either isolate the polypeptide from the culture medium or use the medium containing the polypeptide as such after removal of the cells. It is even possible to use the cells themselves to produce the polypeptide in situ in the process for which the polypeptide having rhamnogalacturonase activity is required. In the preparation of foodstuffs such a host strain that is to be used directly can only be used if it is a food grade host strain.

If the polypeptide is required in extremely purified forms or if particular contaminants are deleterious to the application of the resulting polypeptide, the expression host cell can be selected to avoid such problems. The presence of protease as contaminant for example is not desirable. Presence of protease, in particular, should be avoided when long term storage is being contemplated. It is possible to use size exclusion chromatography involving BioGel P100 (BioRad) to effectively reduce the content of undesirable proteases by 80–90%. In addition to size exclusion chromatography, protease activity can be removed by other well-known techniques such as ion exchange chromatography, bentonite treatment, or pH/temperature inactivation. In order to avoid such costly and complicated steps it is however preferable to select a protease negative strain as host cell.

The subject invention is also directed at a ripening form of a polypeptide with rhamnogalacturonase activity wherein said ripening form is obtainable by expression of the recombinant DNA material according to the invention. In particular a microorganism belonging to the genus *Aspergillus* is a suitable source of a ripening form of a polypeptide with rhamnogalacturonase activity according to the invention. The invention is preferably directed at a mature form of a polypeptide with rhamnogalacturonase activity as no further treatment of said polypeptide is necessary before using said polypeptide in a desired process. In particular the invention is directed at a ripening form of a polypeptide as encoded by a part of the nucleotid sequence of FIG. 9 (sequence listing no. 7). A ripening form of a polypeptide having rhamnogalacturonase activity, said ripening form being encoded by a part of any equivalent nucleotide sequence encoding a polypeptide with an equivalent tertiary structure having rhamnogalacturonase activity also forms part of the invention.

The invention is also directed at a process for producing a ripening form of a polypeptide having rhamnogalacturonase activity comprising culturing a transformed cell previously described in the specification under such conditions that said cell is capable of expressing DNA material capable of producing a ripening form of a polypeptide with rhamnogalacturonase activity and optionally isolating the resulting ripening form of the polypeptide having rhamnogalacturonase activity. The expression of the polypeptide with rhamnogalacturonase activity can be effected by culturing expression host cells that have been transformed with the recombinant DNA material comprising a nucleotide sequence encoding a ripening form of a polypeptide having rhamnogalacturonase activity in a conventional nutrient fermentation medium.

The invention is also directed at a composition comprising a ripening form of a polypeptide having rhamnogalacturonase activity obtainable through expression of recombinant DNA material as disclosed herein or by a process as disclosed herein. Such a composition, which is suitable for:

improving the extraction of soluble solids from vegetable material or for improving the functionality of pectin-containing vegetable material or food material or for the degradation or modification of pectin or pectin-containing vegetable material or plant cell wall material may comprise 0.01–100, preferably 0.1–100 weight % of polypeptide having rhamnogalacturonase activity according to the invention, based on the total weight of polypeptide in the composition.

The invention is also directed at a composition comprising viable, dead or lysed cells comprising a recombinant DNA sequence encoding a ripening form of a polypeptide having rhamnogalacturonase activity as disclosed herein or such cells in any other form or extracts of such cells. Other components capable of the degradation or modification of pectin or pectin-containing vegetable or plant cell wall material may be incorporated in the compositions as disclosed above.

The fermentation medium can comprise an ordinary culture medium containing a carbon source, a nitrogen source, an organic nitrogen source and inorganic nutrient sources. The medium can also contain inducing compounds which activate the expression of the nucleotide sequence encoding a polypeptide having rhamnogalacturonase activity. The selection of the appropriate medium may be based on the choice of expression host and/or based on the regulatory requirements of the recombinant DNA material. Such media are well-known to those skilled in the art. The medium may, if desired, contain additional components favouring the transformed expression host over other potentially contaminating microorganisms. In the-case of production of the polypeptide having rhamnogalacturonase activity for food processing such additional components are necessarily also food grade.

After fermentation the cells can be removed from the fermentation broth by means of centrifugation or filtration. Depending on whether the host cell has secreted the polypeptide having rhamnogalacturonase activity into the medium or whether said polypeptide is still connected to the host cell in some way either in the cytoplasm, in the periplasmic space or attached to or in the membrane or cell wall, the cells can undergo further treatment to obtain the polypeptide.

In the latter case, where the polypeptide is still connected to the cell in some manner, recovery of the polypeptide can for example be accomplished by rupturing the cells for example by high pressure disruption, sonication, enzymatic digestion or simply by cell autolysis followed by subsequent isolation of the desired product. The polypeptide can be separated from the cell mass by various means. In one such method the cells are disrupted by the protease ficin and subjected to ultrafiltration. The polypeptide is subsequently precipitated with an organic solvent such as methanol or acetone. Such isolation methods are well known to a person skilled in the art.

The polypeptide isolated from microbial cells is generally purified by conventional precipitation and chromatographic methods. Such methods include amongst others methanol, ethanol, acetone and ammonium sulfate precipitation and ion exchange and hydroxy apatite chromatography. Such purification methods are well known to a person skilled in the art.

The compositions as disclosed above comprising a polypeptide with rhamnogalacturonase activity may be used in a process requiring the extraction of components from vegetable material or for improving the functionality of pectin or pectin-containing vegetable material, food material or plant cell wall material. Improving the functionality in this respect comprises modifying the properties of vegetable or food material or plant cell wall material in such a way that it may increase the usefulness of the vegetable or food material or plant cell wall material. This increased usefulness may be expressed by a lowered sensitivity to the quality of the raw materials when processing vegetable or plant cell wall material or it may be expressed by an improvement in processing, enhanced productivity etcetera. In this respect, the functionality of products like tea leaves, coffee (beans), flour, dough etcetera may be improved.

The invention is further directed at processes requiring degradation and/or modification of pectin, in particular at processes requiring degradation and/or modification of pectin-containing vegetable or plant cell wall material, in which processes a polypeptide having rhamnogalacturonase activity or a cell capable of expressing such a polypeptide as described above is used.

Rhamnogalacturonase can be an important enzyme in various applications. In addition to the present technical pectolytic and cellulolytic enzymes rhamnogalacturonase can improve liquefaction to the extent that a state of almost complete liquefaction of fruit pulp, resulting in higher extraction yields, can be attained. Rhamnogalacturonase opens the possibility of juice production from tropical fruits, at present a very difficult technology. The invention is therefore in particular directed at industrial processes, such as the liquefaction and/or maceration of fruit pulp and the extraction of juices from plant material. The invention is directed at such processes using any vegetables or fruit such as carrots, apples, grapes, strawberries, tropical fruits and chicory. Furthermore as the interaction between arabinans is considered to be the cause of undesirable haze formation in concentrated fruit and vegetable juices, in particular in apple juice, the use of rhamnogalacturonase alone or in combination with arabinase can prevent haze formation in concentrated fruit and/or vegetable juices as well as in coffee and tea or in fact in any beverages comprising plant material. The use of rhamnogalacturonase alone or in combination with arabinase can also prevent haze formation in brewing processes.

Rhamnogalacturonase alone or in combination with other pectinases and (hemi)cellulolytic enzymes e.g. arabinases can result in new maceration products, which can be used especially in a process for the production of nutritional food preparations or ingredients for foodstuffs, e.g. baby food.

Also the quality of fibrous material containing Rha-GalA poly-(gums) d oligosaccharides (such as present in beet pulp and potato fibers) can be improved by use of rhamnogalacturonase.

Since pectin is an essential part of the plant cell-wall tissue the extraction of oils, gums, natural colours, flavours or flavour precursors from plant biomass can also be facilitated using rhamnogalacturonase optionally in combination with other pectinases and (hemi)cellulolytic enzymes.

The invention is also directed at any products derived from the abovementioned processes. Such products comprise beverages derived from plant material, e.g. fruit juice, coffee, tea, beer, wine, cider and nutritional preparations and ingredients for foodstuffs, e.g. for baby food and new maceration and/or liquefaction products.

BRIEF DESCRIPTION OF TABLES AND FIGURES

Table 1: Viscosity reduction in apple hot mash experiments. 1. Addition of Biopectinase LQ at 500 g/tonne. 2. As 1+addition of rhamnogalacturonase containing fermentation broth from *A. aculeatus* CBS 115.80

Table 2: Volume (ml), Brix, % Yield at 10.4 Brix, pH and pectin test of a centrifuged 30 g apple hot mash sample 2 hours after incubation with 1. Biopectinase LQ at 500 g/tonne. 2. As 1+addition of rhamnogalacturonase containing fermentation broth from *A. aculeatus* CBS 115.80. 3. No enzymes added.

FIG. 1: Dionex BioLC/HPAE chromatogram of isolated Modified Hairy Regions without addition of enzymes (A,B), after incubation with Biopectinase (C,D) and after incubation with Biopectinase+rhamnogalacturonase containing fermentation broth from *Aspergillus aculeatus* (E,F). Entire chromatogram shown left, detail of 20–35 minutes retention time shown right.

Figure 2:
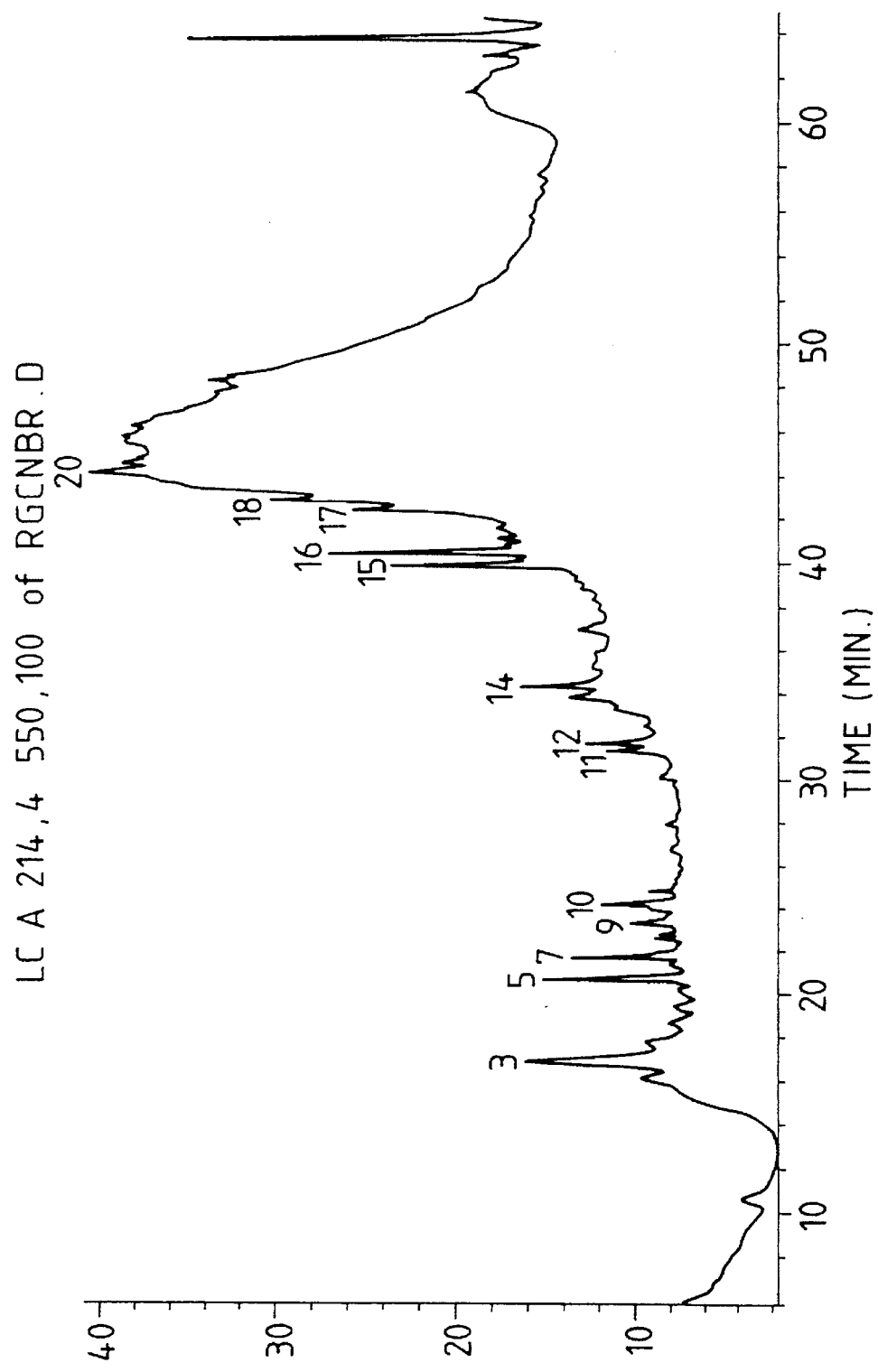

FIG. 2: Elution profile of HPLC separation of rhamnogalacturonase CNBr fragments from *Aspergillus aculeatus*.

FIG. 3: Partial amino-acid sequence of fragments of *Aspergillus aculeatus* rhamnogalacturonase generated by cleavage with cyanogen bromide (CNBr fragment #7 and #15) and after cleavage with Endoproteinase Lys-C (Elys fragment #7 and #5).

Figures 4, 5:
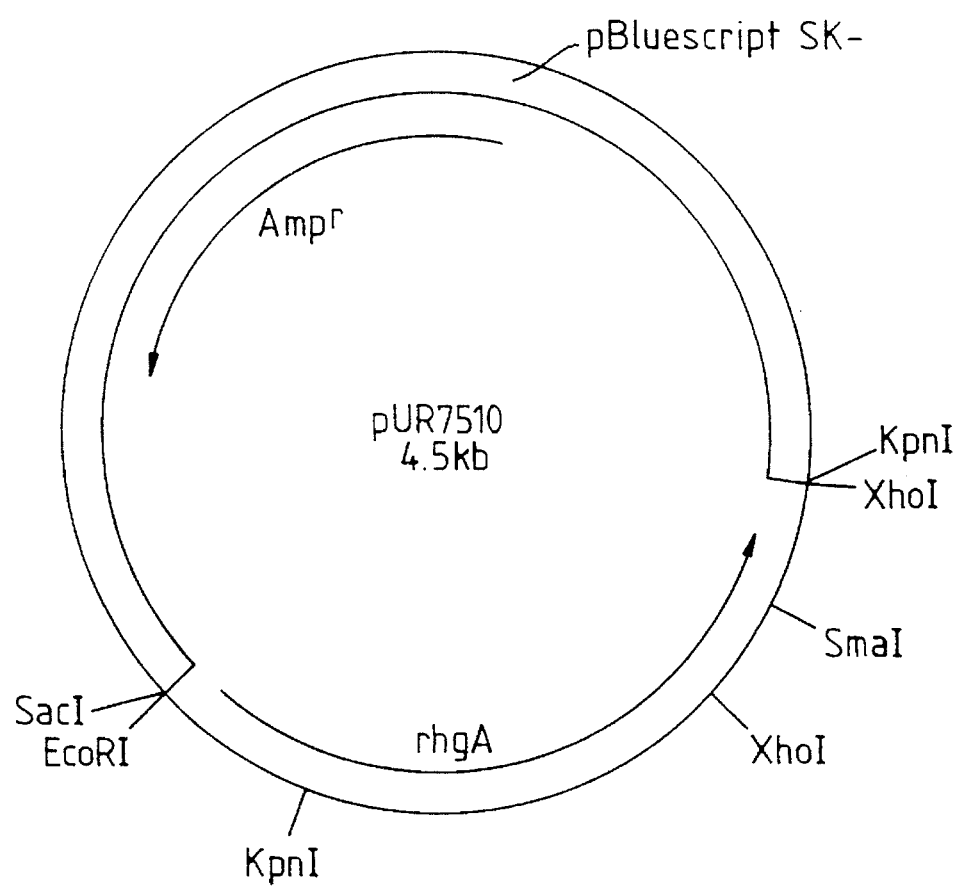

FIG. 4: Western blot analysis, using rhamnogalacturonase antibodies, of supernatant of *Aspergillus aculeatus* fermentation broth at several hours after a switch (at t=0) from sucrose to apple pectin. Lanes indicate hours after transfer.

FIG. 5: Map of plasmid pUR7510, containing a cDNA fragment comprising the entire coding region of the *Aspergillus aculeatus* rhamnogalacturonase gene (rhgA).

FIGS. 6A–6F: Nucleotide sequence of a cDNA copy of the *Aspergillus aculeatus* rhamnogalacturonase gene (rhgA) and amino acid sequence derived therefrom.

FIG. 7: Restriction map of the genomic DNA of *Aspergillus aculeatus* in the region of the rhamnogalacturonase gene.

FIG. 8: Map of plasmid pUR7511, containing a genomic DNA fragment comprising the *Aspergillus aculeatus* rhamnogalacturonase gene.

FIGS. 9A–9I: Complete nucleotide sequence of the *Aspergillus aculeatus* rhamnogalacturonase gene (rhgA), including flanking regions, and amino acid sequence derived therefrom.

Figure 10A:
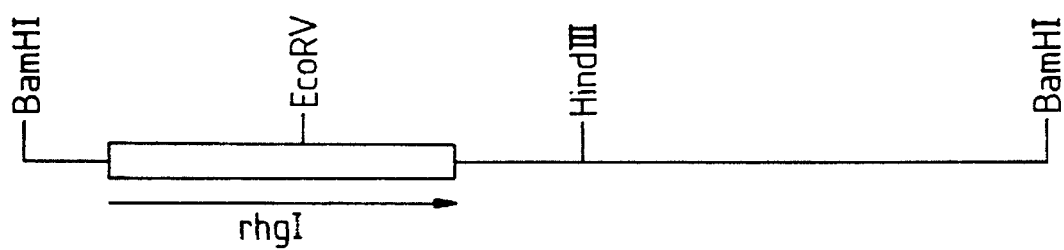
Figure 10B:
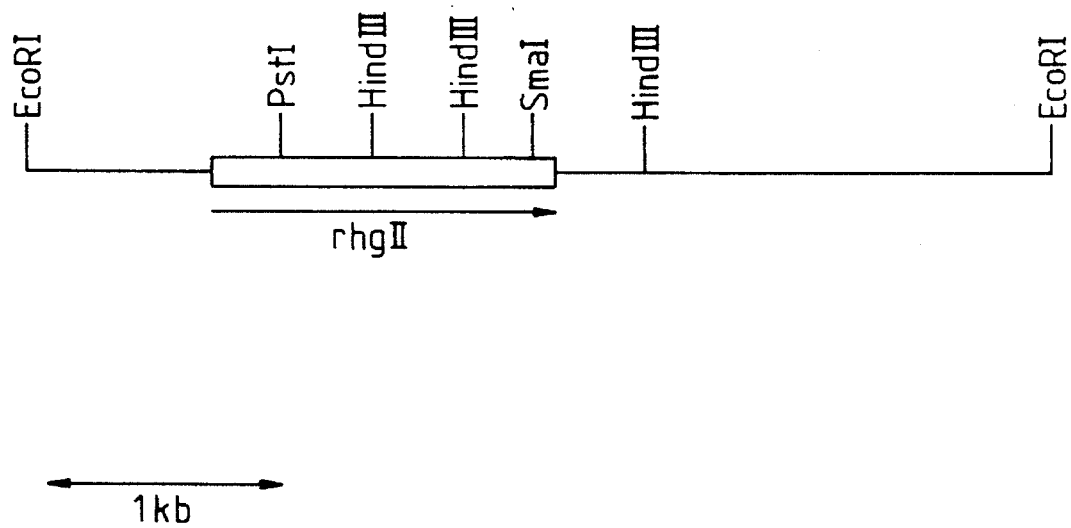

FIG. 10: Restriction map of the genomic DNA of *Aspergillus niger* in the region of A) rhgl (4.5 kb BamHI fragment) and B) rhgII (4.5 kb EcoRI fragment).

Figure 11:
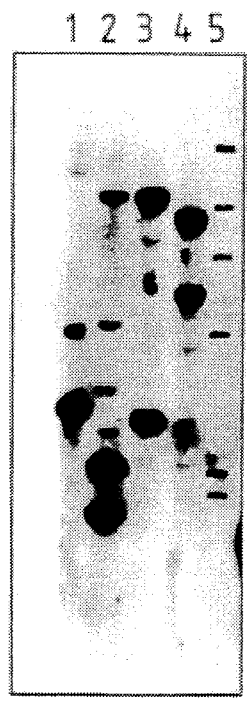

FIG. 11: Southern analysis of *Aspergillus niger* and *Aspergillus aculeatus* genomic DNA after digestion with BamHI and EcoRI with the 2.5 kb BamHI- HindIII fragment of rhgl from *Aspergillus niger* as probe. *A. aculeatus* genomic DNA lane 1 (BamHI digestion) and lane 2 (EcoRI digestion). *A. niger* genomic DNA lane 3 (BamHI digestion) and lane 4 (EcoRI digestion). Lane 5: Marker.

Figure 12:
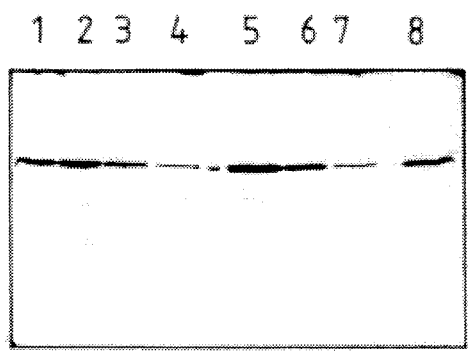

FIG. 12: Western blot analysis, using rhamnogalacturonase antibodies, of supernatant of *Aspergillus aculeatus* transformants 75 (lane 2, lane 3 (5 times diluted) and lane 4 (25 times diluted) and transformant 67 (lane 5, lane 6 (5 times dilution) and lane 7 (25 times dilution) and wild type *Aspergillus aculeatus* 115.80. (lane 1,8)

Figure 13:
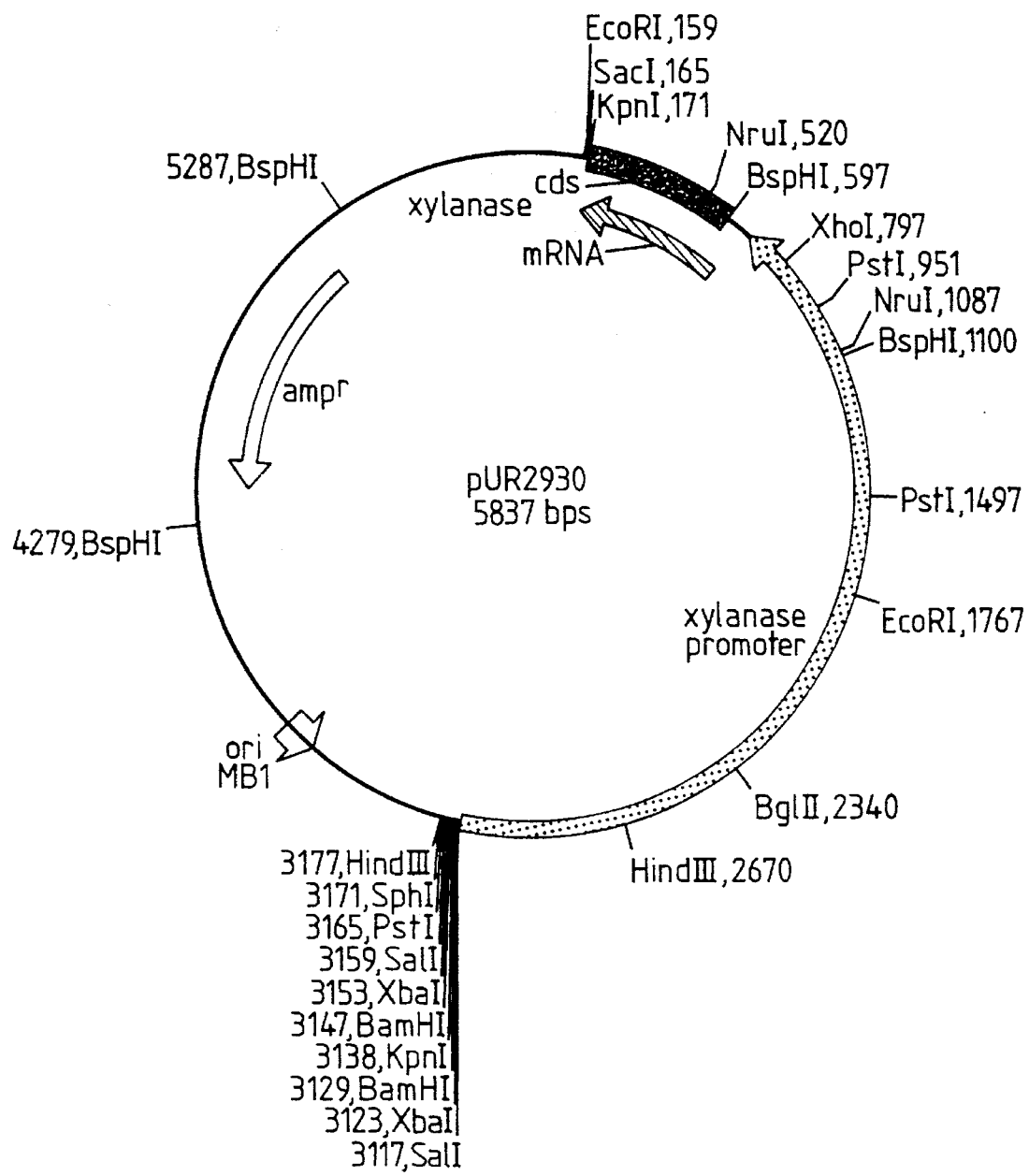

FIG. 13: Map of plasmid pUR2930, comprising the promoter region of the *Aspergillus niger var. awamori* xylA gene.

Figure 14:
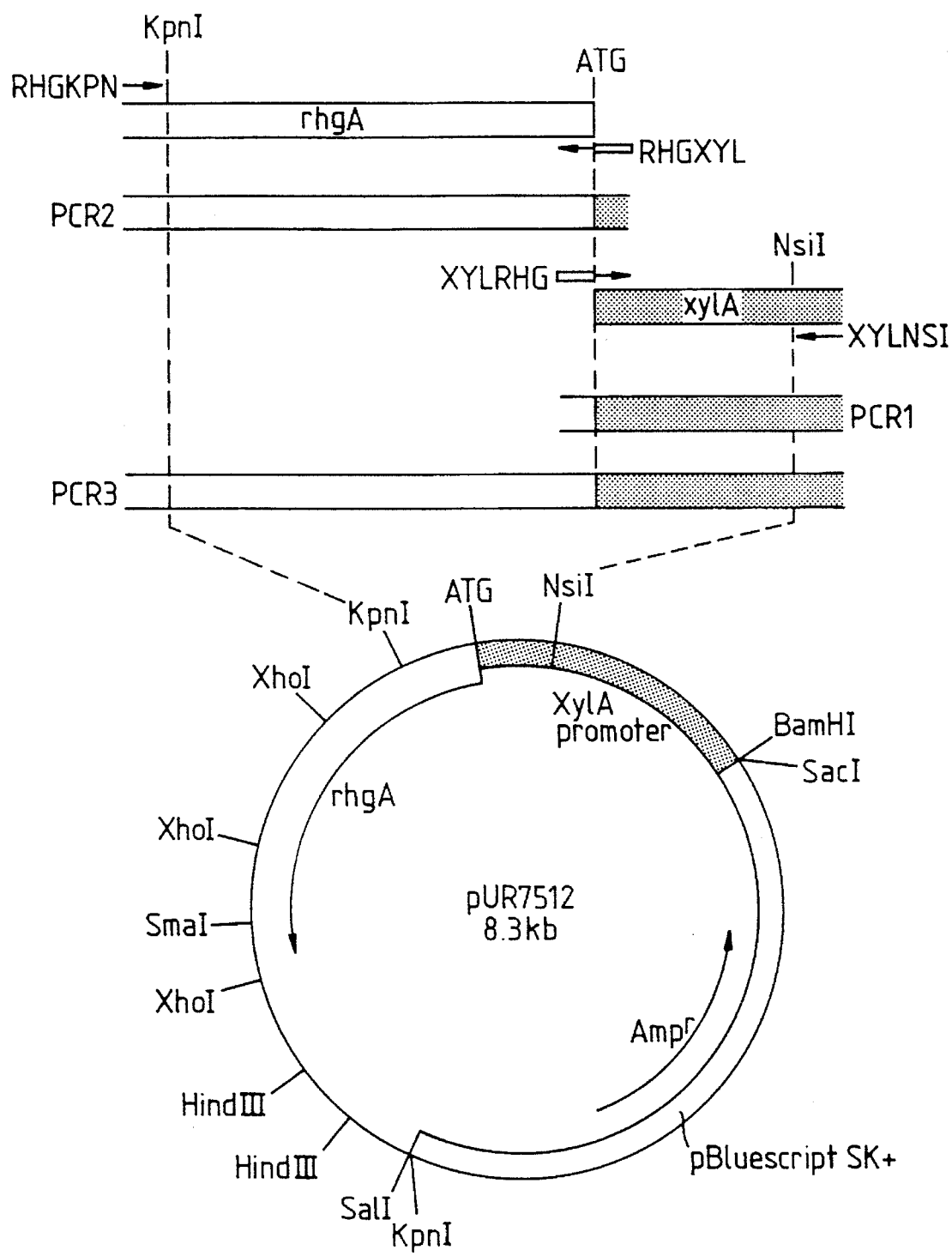

FIG. 14: Schematic representation of the construction pathway for a plasmid comprising the rhgA gene of *Aspergillus aculeatus* under the control of the xylA promoter of *Aspergillus niger var. awamori* by means of PCR.

Figure 15:
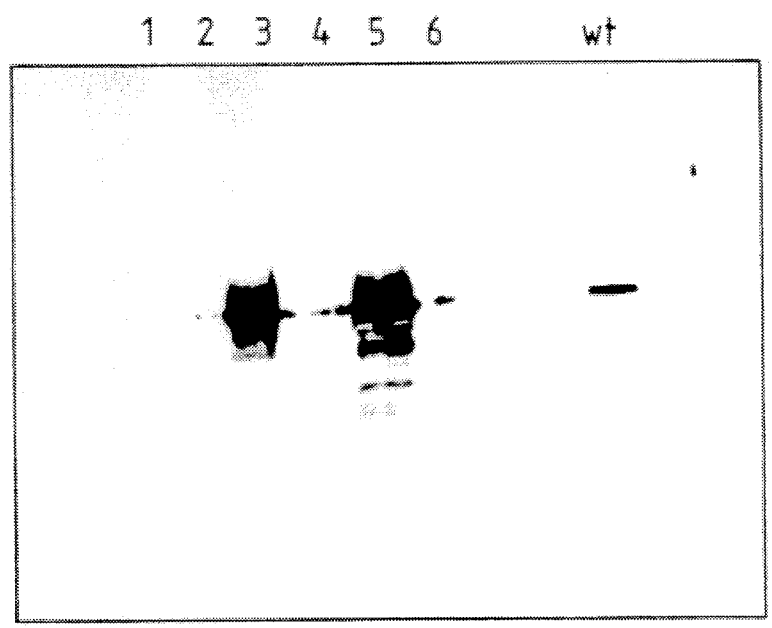
Figure 16A:
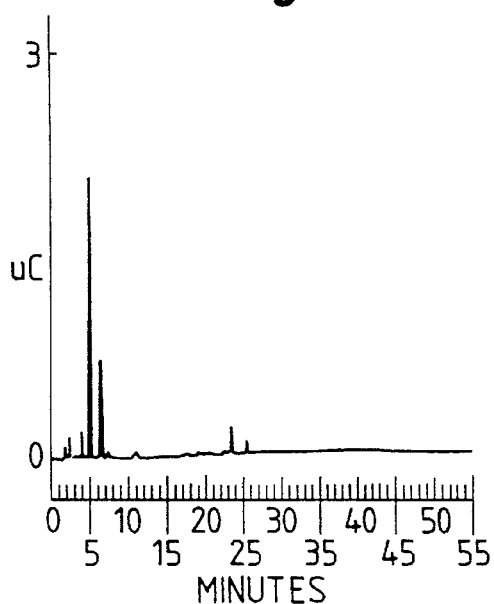
Figure 16B:
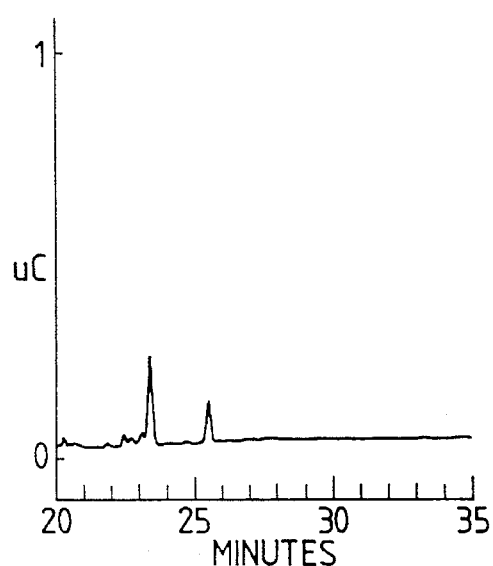
Figure 16C:
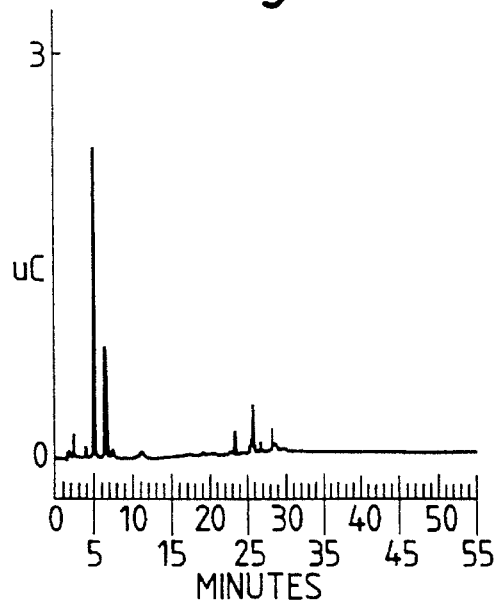
Figure 16D:
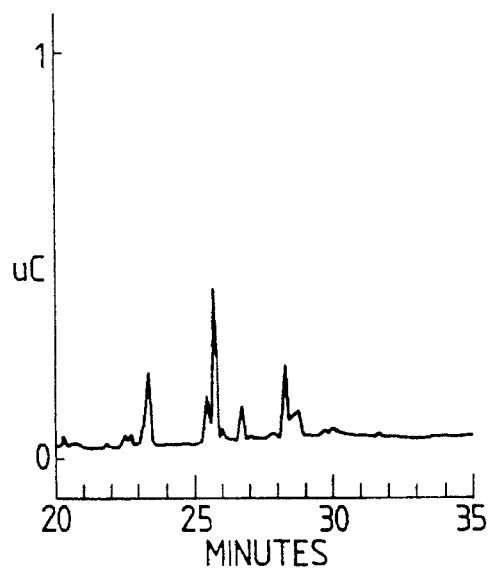

FIG. 15: Western blot analysis, using rhamnogalacturonase antibodies, of supernatant of 6 transformants of *Aspergillus niger var. awamori* containing the *A. aculeatus* rhamnogalacturonase gene under the control of the *A. niger var. awamori* xylA promoter (lane 1 until 6) and *A. aculeatus* wild type (wt) supernatans induced on apple pectin.

FIG. 16: Dionex BioLC/HPAE chromatogram of isolated Modified Hairy Regions without addition of enzymes (A,B) and after incubation with rhamnogalacturonase containing fermentation broth from *Aspergillus niger var. awamori* containing the *A. aculeatus* rhamnogalacturonase gene under the control of the *A. niger var. awamori* xylA promoter (B). Entire chromatogram shown left, detail of 20–35 minutes retention time shown right.

Figure 17:
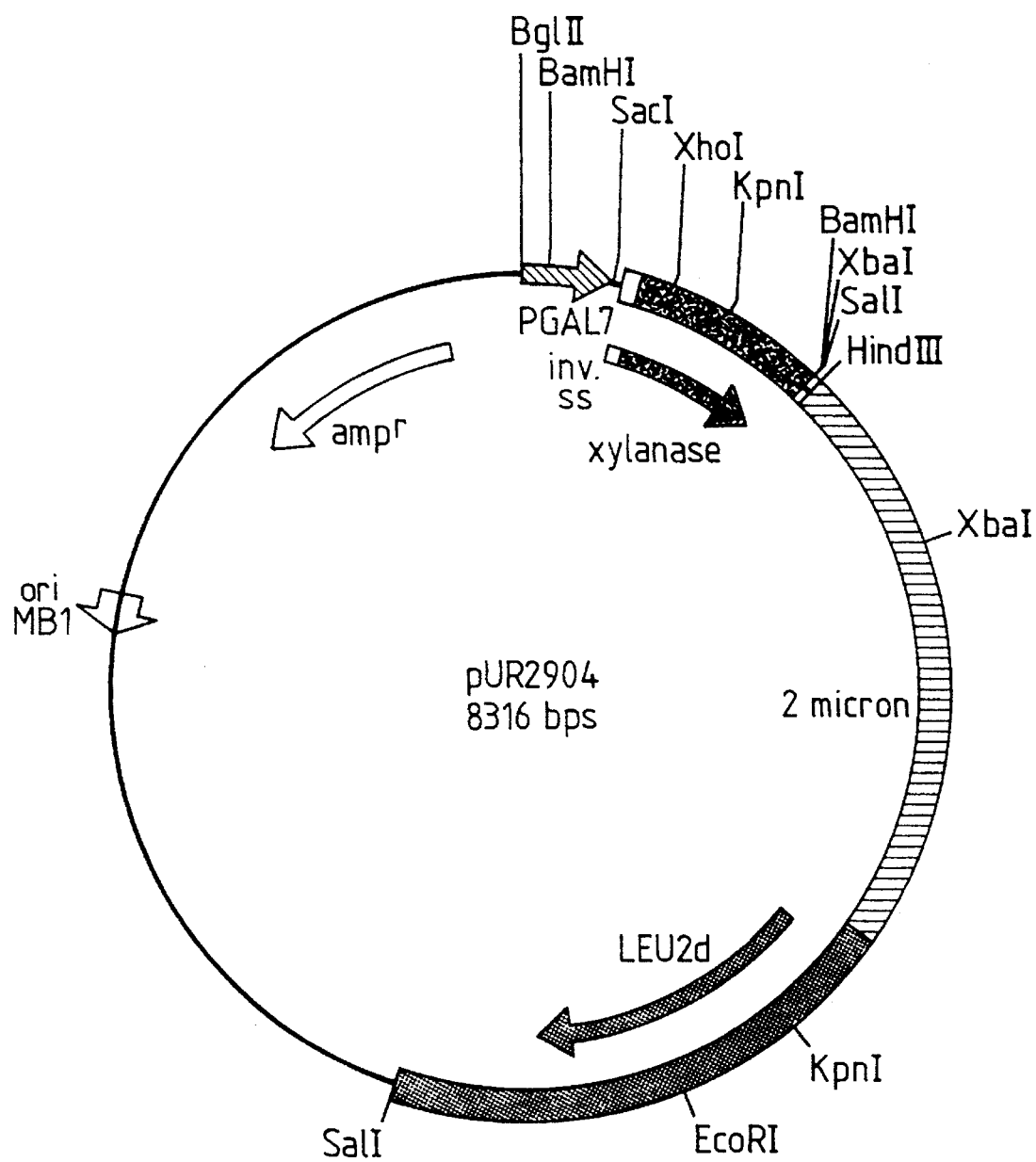

FIG. 17: Map of plasmid pUR2904, an *Escherischia coli—Saccharomyces cerevisiae* shuttle vector.

Figure 18:
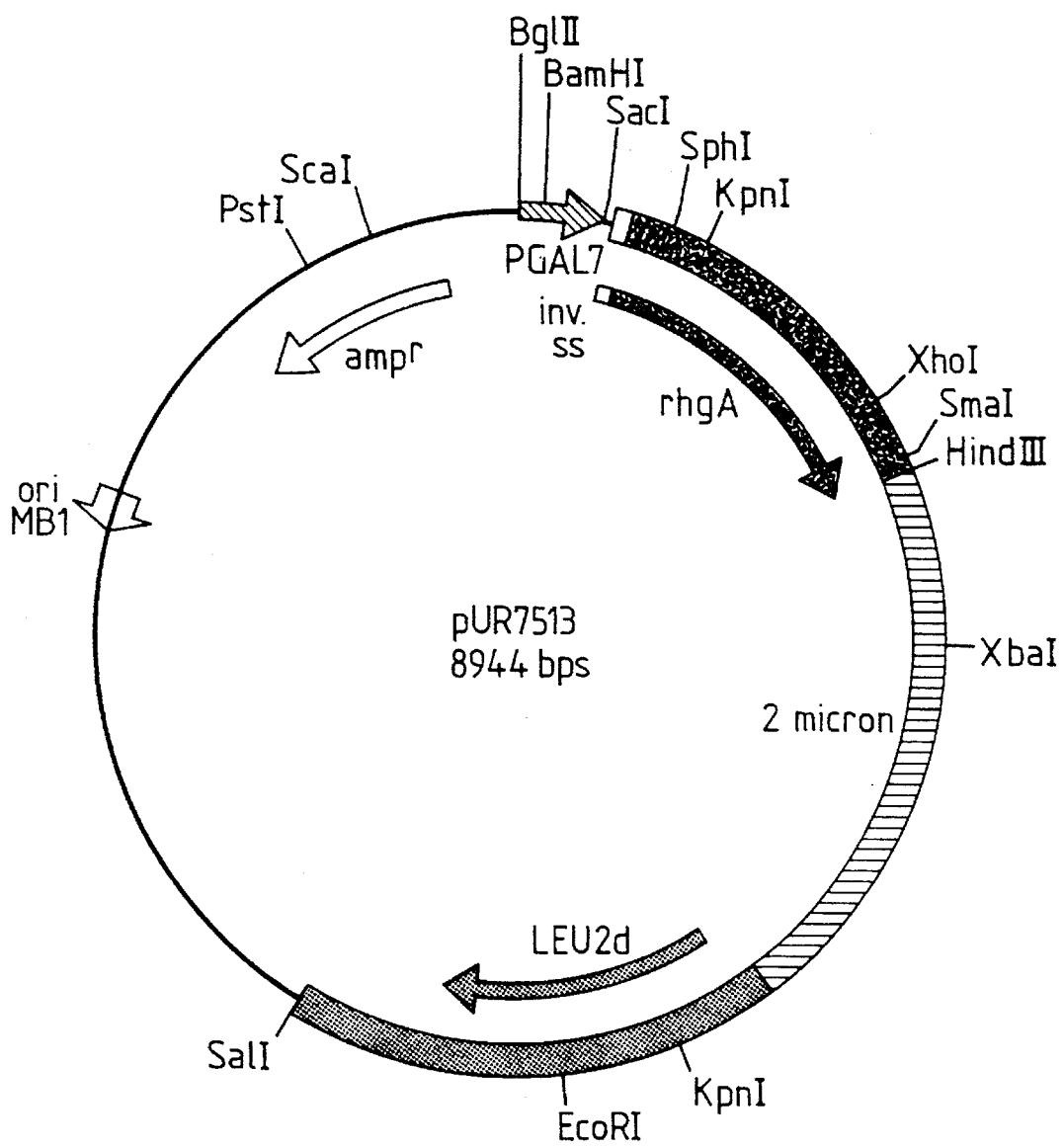

FIG. 18: Map of a plasmid (pUR7513), comprising the *Saccharomyces cerevisiae* invertase signal sequence and the rhgA gene of *Aspergillus aculeatus* under the control of the gal7 promoter of *Saccharomyces cerevisiae*.

EXAMPLE 1

Use of rhamnogalacturonase from *Aspergillus aculeatus* in apple juice manufacturing 1.1. Production of rhamnogalacturonase by *Asperillus aculeatus*

1.1.1. Isolation of rhamnogalacturonase and preparation of antibodies

Rhamnogalacturonase was isolated using the method and the commercial preparation described by Schols et al. (1990a). The purified rhamnogalacturonase was used for the immunisation of two mice using the method described by van der Veen et al. (1991). The antibodies obtained were used for screening and purification of rhamnogalacturonase from *Aspergillus aculeatus*.

1.1.2. Identification of strains of filamentous fungi producing rhamnogalacturonase Various strains of different species of filamentous fungi were cultured in 50 ml conical shake flasks in order to compare their natural production levels of rhamnogalacturonase. The working volume was 30 ml, containing a medium of the following composition:10 gram sugar beet pulp in 1 liter minimal medium containing 6 gram $NaNO_3$, 0.5 gram KCl, 1.5 gram $KH_2PO_4$, 0.9 ml 10 N KOH, 0.5 gram $MgSO_2.7$ $H_2O$ and 1 ml of a 1000×concentrated trace element solution according to Visniac and Santer (1957). Shake flasks were incubated with spores (10E6/ml) and incubated for 48 hours at 30° C. onase gene under the control of the *A. niger var. awamori* xylA promoter (B). Entire chromatogram shown leftfiltrate was analysed by SDS PAGE gel electrophoresis followed by Western blotting (Burnette 1981). Loading buffer (4 times loading buffer contains 1.25 M Tris/HCl pH 6.8, 10% sodium dodecyl sulphate, 20% 2-mercapto ethanol, 50% glycerol and 50 ug/ml bromophenol blue) was added to the culture filtrate and the samples were boiled for 5 minutes prior to loading onto the gel. Western blots were analysed for cross-reactivity with antibodies raised against purified rhamnogalacturonase. Various strains of Aspergillus showed 1 distinct band after hybridisation with rhamnogalacturonase antibodies, with molecular weights ranging from 51000 D–63000 D. The following strains were able to secrete a protein showing cross reactivity with rhamnogalacturonase antibodies: *Aspergillus japonicus* (CBS 114.51, CBS 621.78), *Aspergillus aculeatus* (CBS 115.80, CBS 172.66, CBS 119.49), *Aspergillus niger* 402 (CBS 120.49), *Aspergillus niger hennebergi* (CBS 117.80), *Aspergillus niger intermedius* (CBS 559.65), *Aspergillus niger nanus* (CBS 136.52, CBS 117.48), *Aspergillus foetidus* (CBS 121.78, CBS 618.78), *Aspergillus carbonarius* (CBS 112.80, CBS 420.64). Consequently the antibodies raised against rhamnogalacturonase can be used to screen microorganisms for the synthesis of rhamnogalacturonase. The organisms described above contain a gene encoding a protein which shows cross reactivity with antibodies raised against rhamnogalacturonase and therefore can be used to isolate such a gene and, in principle, can be used for the overproduction of rhamnogalacturonase.

1.1.3. Rhamnogalacturonase production by *Aspergillus aculeatus* CBS 115.80 and CBS 172.66 on several substrates.

Since the absolute amount of rhamnogalacturonase produced under the conditions described above was rather low, *Aspergillus aculeatus* CBS 115.80 and CBS 172.66 were used in shake flasks experiments in order to compare the production of rhamnogalacturonase on several substrates. Strains were grown as described above on minimal medium and 5 g/l Difco yeast extract, 2 g/l casamino acids and 30 g/l sucrose. After growth for 24 hours cells were harvested by centrifugation and resuspended in minimal medium and 10 gram per liter of the tested substrate. Cross reactivity with antibodies raised against rhamnogalacturonase was found after transfer to rhamnose (20 gram/liter) in combination with galacturonic acid (20 gram per liter) and on apple pectin, citrus pectin, beet pectin and sugar beet pulp. No cross reactivity with antibodies raised against rhamnogalacturonase was found after transfer to media containing simple carbon sources such as sucrose, glucose, fructose, rhamnose or galacturonic acid. Transfer to lower ratios of rhamnose/galacturonic acid (1:2, 1:5 and 1:10, based on 20 gram per liter galacturonic acid) also resulted in rhamnogalacturonase production. It is clear that rhamnogalacturonase is not produced constitutively but that growth conditions determine the expression of the rhamnogalacturonase gene.

1.1.4. Fermentative production of rhamnogalacturonase *Aspergillus aculeatus* CBS 115.80 and CBS 172.66

*Aspergillus aculeatus* CBS 115.80 and CBS 172.66 were cultured in Chemoferm glass 10 liter fermenters equipped with a magnetically driven eight blade impeller. The dissolved oxygen tension was measured with an Ingold oxygen probe, the pH was determined with an Ingold pH electrode and the temperature was measured using a PT100 sensor. The working volume of the fermenter was 8 liter. Applikon ADI 1020 control units were used for control of pH, temperature, pO2, gass inlet (3 l/min) and stirrer speed (600–1000 rpm). During the fermentation the pH was kept at 4.5 by the addition of a 12.5% ammonia solution and the temperature was kept at 30° C. Fermenters were inoculated with 300 ml of a germinated spore suspension (final concentration 10E6/ml). Spores were germinated for 6 hours at 30° C. in a shaking incubator in the minimal medium described above.

*Aspergillus aculeatus* CBS 172.66 and CBS 115.80 were cultured according to the method described on minimal medium with 10 gram/liter sucrose as carbon source. After growth of the fungus by consumption of sucrose a feed of rhamnose (0.2 gram/liter/hour) and galacturonic acid (0.4 gram/liter/hour) was connected. Rhamnogalacturonase was detected 3 hours after connection of the feed, as judged by Western analysis of the supernatant with the rhamnogalacturonase antiserum. Two days after start of the fed-batch the fermentations were stopped and fermentation broth, obtained after filtration of the biomass, was concentrated 10 times using an asahi hollow fiber kidney. The concentrated fermentation broth was again analysed for the presence of rhamnogalacturonase by Western blot analysis and used in activity tests on modified hairy regions.

In another fermentation experiment *Aspergillus aculeatus* CBS 115.80 was cultured according to the method described on minimal medium containing 5 grams/liter sucrose, 5 grams/liter apple pectin and 5 grams/liter citrus pectin. The fermentation process was carried out for 72 hours, followed by filtration of the biomass and concentration of the fermentation liquid as described above. The concentrated fermentation broth contained rhamnogalacturonase, as judged by Western blot analysis with the rhamnogalacturonase antibodies and was used in activity tests on modified hairy region and in apple hot mash application trials.

1.2. Activity of rhamnogalacturonase from *Aspergillus aculeatus* in apple juice manufacturing 1.2.1. Activity of rhamnogalacturonase from *Aspergillus aculeatus* on modified hairy regions For the isolation of modified hairy regions, Golden Delicious apples (10 kg) were crushed in a Magimix Cuisine Systeme 3000 and treated with an enzyme preparation (Biopectinase 200 L 0.05%) from Quest International for 4 hours at 55° C. After centrifugation (Sorvall RC-5B) at 8000 g for 30 minutes the supernatant was ultrafiltered and concentrated in a Pellicon microfiltration unit having a molecular weight cut off of 50.000. The residue was dialysed and lyophilized.

The isolated polysaccharide was characterised by analyzing enzymatic degradation products. 5 ml of 0.2% solutions of the isolated Modified Hairy Regions in 0.05 M sodium acetate buffer (pH=5.0) were incubated with 10 µl enzyme preparations for 2 hours at 50° C. Analysis of the formed products was performed on a Dionex BioLC/HPAE chromatography system or by measuring the increase in the reducing end-groups making use of the DNS method. The Dionex system uses a Carbo Pac PA-1 anion exchange column (25 cm, 4 mmi.d.) and a CarboPac PA-1 Guard. The column was loaded with 25 µl of the solution (0.2%) and eluted with a linear gradient of 0–0.5 M NaOAc in 0.1 N NaOH during 50 minutes. The flow rate was 1.0 ml/min and the process was monitored using a PE detector.

For the reducing end group method the DNS reagent was prepared as follows: 20.0 grams of 2-hydroxy-3,5 dinitrobenzoic acid (Merck 800141) was suspended in 400 ml distilled water. With continuous magnetic stirring, 300 ml of NaOH solution (32 grams in 300 ml distilled water) was gradually added to this suspension. The solution was warmed cautiously to 45° C. until it was clear. Rochelle salt (600 g, K-Na-tartrate, Merck 8087) was added under continuous stirring. The solution was diluted to 2000 ml with distilled water and stored in a dark bottle at room temperature. Using the DNS method, 0.5 ml of the reaction mixture (MHR and enzyme preparation after 2 hours of incubation as described above), was added to 1.5 ml demi-water and 2 ml DNS-solution. The solution was boiled for 10 minutes and after cooling to room temperature the extinction was measured at 543 nm.

FIG. 1 shows the Dionex pattern of isolated Modified Hairy Regions without the addition of enzymes (FIG. 1a), incubated with Biopectinase OS (1C), and incubated with 10 μl rhamnogalacturonase containing fermentation broth from *Aspergillus aculeatus* CBS 115.80 cultured on a combination of sucrose, apple pectin and citrus pectin as described above (1E). It is clear that the isolated Modified Hairy Regions can only be degraded by rhamnogalacturonase containing fermentation broth and not by Biopectinase (containing other pectinases e.g. polygalacturonases, pectinesterases and petin transeliminases).

Using the DNS method the reducing sugars obtained after incubation of the modified hairy regions with 10 μl rhamnogalacturonase containing fermentation broth from *Aspergillus aculeatus* CBS 115.80 cultured on a combination of sucrose, apple pectin and citrus pectin as described above resulted in an extinction of 1.06 at 543 nm. Addition of rhamnogalacturonase containing fermentation broth after fed batch cultivation on rhamnose and galacturonic acid as described above resulted in a extinction of 0.52 at 543. Biopectinase was used in this method as a control resulting in extinctions of 0.32 at 543 nm.

Modification of the isolated Modified Hairy Regions with endoarabinase or with arabinofuranosidase did not result in futher degradation monitored either by the DNS method or by the Dionex system. Consequently rhamnogalacturonase containing fermentation broth from *Aspergillus aculeatus* CBS 115.80 showed good activity in the degradation of modified hairy regions due to the activity of rhamnogalacturonase. The highest activity was found after cultivation on pectin based media.

1.2.2. Use of rhamnogalacturonase from *Aspergillus aculeatus* in apple juice manufacturing Apples were peeled, chopped, depipped and mashed to a fine puree. Apple mash was distributed into 500 g aliquots and preincubated at 55° C. The mashes were treated with enzyme preparation as shown below and incubated for 2 hours at 55° C. Viscosity of mash was measured several times using a Brookfield viscometer with Helipath stand attachment and T bar spindle. After 2 hours of incubation a 30 g sample was removed from each mash and centrifuged for 20 minutes at 10.000 rpm. The volume, pH and Brix of the juice were measured. The pectin level of the juice was assessed by a standard alcohol test (1 part juice/2 parts isopropanol). Concentrated fermentation broths were tested in the presence of Biopectinase LQ, containing cellulases and various pectinases. The results of a typical experiment in which 3 ml of a concentrated rhamnogalacturonase containing fermentation broth from a sucrose/pectin fermentation of *Aspergillus aculeatus* CBS 115.80 was evaluated is shown in Table 1 and 2. It is clear that the addition of the rhamnogalacturonase containing broth resulted in an improved viscosity reduction of the mash especially in the early stages of incubation. Also a significant increase in juice brix and juice yield was observed. Inclusion of rhamnogalacturonase containing fermentation broth resulted in a lowering of juice pH and a clearer juice containing less pectin material. Considering the observed activity of rhamnogalacturonase from *Aspergillus aculeatus* on modified hairy regions and the performance in application trials this species was used as starting material for the isolation of the rhamnogalacturonase gene.

TABLE 1

Time course of viscosity reduction (cps) in apple hot mash experiments: Effect of rhamnogalacturonase in addition to Biopectinase LQ. T = time in minutes

|  | T = 0 | T = 15 | T = 30 | T = 60 | T = 120 |
|---|---|---|---|---|---|
| Biopectinase | 55692 | 17745 | 8034 | 7098 | 5518 |
| Biopectinase + rhamnogalacturonase | 55692 | 11407 | 6942 | 5440 | 5525 |

TABLE 2

Volume, brix, yield, pH and cloudiness after centrifugation of 30 gram apple hot mash, incubated for 2 hours with various enzymes.

|  | volume (ml) | Brix | % yield at 10.4 brix | pH | pectin test |
|---|---|---|---|---|---|
| Biopectinase | 24 | 11.3 | 86.9 | 3.66 | hazy |
| Biopectinase + rhamnogalacturonase | 25 | 11.8 | 94.5 | 3.60 | clear |
| No enzymes added | 23 | 10.4 | 76.6 | 4.05 | gel |

EXAMPLE 2

Cloning and analysis of the *Aspergillus aculeatus* rhgA gene 2.1. Identification of partial amino acid sequences of *A. aculeatus* rhamnogalacturonase 2.1.1. Isolation of rhamnogalacturonase from *Aspergillus aculeatus* 172.66

*Aspergillus aculeatus* CBS 172.66 was cultured in a 10 liter fermenter according to the method described above on minimal medium supplemented with 5 grams per liter peptone and 10 grams per liter sugar beet pulp. After 50 hours of cultivation cells were removed by filtration through miracloth filters and the culture filtrate was used for the purification of rhamnogalacturonase. Culture filtrate was diluted 5 times with water and brought to pH 6.5 with NaOH after which DEAE Sephadex-A50 (20 g/l), equilibrated in 20 mM sodium phosphate buffer pH 6.5, was added. The suspension was mixed for two hours and the DEAE Sephadex-A50 was collected on a glass funnel. The bound protein was eluted in steps with 0.5 M NaCl and 20 mM sodium phosphate buffer pH 6.5 and was collected in fractions. The rhamnogalacturonase containing fractions were identified by SDS-PAGE followed by Western blotting using the rhamnogalacturonase antibodies described above. The rhamnogalacturonase containing fractions were dialysed against distilled water and loaded on a DEAE Sepharose Fast Flow column (dimensions 2.6×9 cm) equilibrated with 20 mM piperazine/HCl buffer pH 6.0 and eluted with a 1000 ml NaCl gradient (0–0.5 M) in the same buffer. The collected fractions were analysed by Western blotting for rhamnogalacturonase as described above and L-arabinofuranosidase B (exo-B) activity by the method described by van der Veen et al (1991), since exo-B is known to co-elute with rhamnogalacturonase (Schols et al 1990a). To remove the exo-B the rhamnogalacturonase containing fractions were dialysed against 5 mM piperazine/HCl buffer pH 6.0 and reloaded on the same DEAE Sepharose Fast Flow column and eluted with 1000 ml NaCl gradient (0–0.3 M) in the same buffer. Further purification of rhamnogalacturonase involved fractionation using a Pharmacia (Pharmacia, Uppsala Sweden) FPLC system equiped with a MONO-P HR 20/5 column (Pharmacia) equilibrated in 20 mM piperazine/HCL buffer pH 6.0. The column was eluted with 10% polybuffer74 (Pharmacia)/HCl pH 3.5. The fractions containing the highest rhamnogalacturonase concentrations as determined by Westernblot were pooled, the pH was brought to pH 6.0 with HCl and reloaded on the MONO-P HR 20/5 column. The column was eluted with 8% polybuffer74/HCl pH 3.5. Further purification of rhamnogalacturonase was done by using a Superose 12 column (dimensions 1.6*64 cm) equilibrated in 0.1 M sodium acetate buffer pH 5.5 and 0.1 M NaCl. The column was eluted with the same buffer. The collected fractions, containing the purified rhamnogalacturonase, were analysed by SDS-PAGE and Western blotting, resulting in one distinct band, showing cross reactivity with the rhamnogalacturonase antibodies.

2.1.2 Determination of the N-terminal amino acid sequence of *A. aculeatus* rhamnogalacturonase The pure rhamnogalacturonase fraction was used for determination of the N-terminal amino acid sequence of rhamnogalacturonase from *A. aculeatus* CBS 172.66, using the sequential degradation method of Edman and an Applied Biosystems Sequencer Model 475 with an on-line PTH-analyzer model 120A. Although various amounts of purified protein and varying conditions were employed, the N-terminal residue(s) of *A. aculeatus* rhamnogalacturonase could not be identified. It was concluded that *A. aculeatus* extracellular rhamnogalacturonase resists Edman degradation of the N-terminus, and consequently probably is modified at the N-terminus. Such modifications are rarely encountered in extracellular proteins, though some cases have been described, in which the modification is derived from rearrangement of an N-terminal glutamine residu, yielding a pyroglutamic acid group. Thus, the N-terminal amino acid residu of *A. aculeatus* rhamnogalacturonase presumably is a glutamine.

2.1.3. Determination of amino acid sequences of internal regions of *A. aculeatus* rhamnogalacturonase The purified rhamnogalacturonase fraction was used to generate fragments of the rhamnogalacturonase polypeptide by cleavage with CNBr essentially according to Gross and Witkop (as described in "Sequencing of Proteins and Peptides", G. Allen, Laboratory Techniques in Biochemistry and Molecular Biology, Ed. T. S. Work and R. H. Burdon, 1981). The fragments were separated by HPLC, using a Bakerbond C4 wide pore column (5 μm; 4.6*250 mm) (FIG. 2). The fractions corresponding to peaks 7 and 15 of the elution profile were named CNBr fragment #7 (sequence listing no. 1), resp. CNBr fragment #5 (sequence listing no. 2), and were subjected to amino acid sequence analysis according to the method of Edman (FIG. 3, sequence listing no. 1 and no. 2). Another set of fragments of the rhamnogalacturonase polypeptide was obtained by cleavage with Endoproteinase Lys-C (Boehringer, Mannheim), essentially as described by Aitken et al. (1989). The fragments were separated by HPLC, using a Bakerbond C4 wide pore column (5 μm; 4.6*250 mm) and selected fractions Endolys#5 (sequence listing no. 4), Endolys#7 (sequence listing no. 3) were subjected to amino acid sequence analysis according to the method of Edman (FIG. 3, sequence listing no. 3 and no. 4).

2.2. Isolation and characterization of cDNA of the *A. aculeatus* rhgA gene

All techniques used for the manipulation and analysis of nucleic acid materials were performed essentially as described in Maniatis et al. (1982), except where indicated otherwise.

2.2.1 Construction and screening of an expression library

*A. aculeatus* CBS 115.80 was grown in a 2.5 liter fermenter (working volume 2 liter) as described in chapter 1.1.4. on minimal medium (pH=6 regulated with KOH) supplemented with 1% sucrose, 0.2% yeast extract and 0.2% casamino acids. After 24 hours of growth cells were removed by filtration on miracloth, washed twice in minimal medium and resuspended in the original volume of minimal medium supplemented with 1% apple pectin (brown ribbon apple pectin (degree of esterification 72.8%), obipectin, pH=4, regulated with KOH) as a carbon source. Strong induction of the rhamnogalacturonase gene was observed in less then 6 hr after the shift, as judged by Western analysis of the supernatant with the rhamnogalacturonase-antiserum (FIG. 4). Therefore, total RNA was isolated 3, 6 and 24 hr after shifting from sucrose medium to 1% apple pectin using the guanidinium thiocyanate method and purified twice by cesium chloride density gradient centrifugation, essentially as described by Maniatis et al. (1982). Total RNA isolates derived at different moments in time were pooled and a polyA$^+$ fraction (mRNA) was isolated using a polyATtract mRNA isolation kit (Promega). This mRNA fraction was used for the construction of a cDNA library using a ZAP cDNA synthesis kit (Stratagene, La Jolla) according to the instructions of the supplier, yielding cDNA fragments with a XhoI cohesive end flanking the poly-A region and an EcoRI adaptor at the other end. The obtained cDNA fragments were used for directional cloning in the sense orientation in lambda ZAPII vectors (Stratagene, La Jolla), allowing expression of β-galactosidase fusion proteins (Huse et al., 1988). In order to increase the sensitivity of the screening procedure, the inserts were excised from the lambda-vectors as phagemids by infection with helper phage R408 (Stratagene, La Jolla) and packaged phagemid particles were isolated from the culture according to the instructions of the supplier. The obtained mixture of pBluescript SK-phagemids was used to infect *E.coli* BB4 (Stratagene, La Jolla) and cells were plated on LB-Amp selection plates. The obtained colonies were transferred to nitrocellulose filters (Schleicher & Schüell, presoaked with a 10 mM IPTG solution); filters were placed on LB plates, containing ampicillin and 10 mM IPTG (colony side up), and were incubated for 3 hours at 37° C. to induce expression of β-galactosidase fusion proteins. The filters were lifted from the plates and subjected to the following treatment: soaking for 3 minutes in 0.5 M NaOH and 8 M urea (cell lysis, denaturation of all proteins), followed by soaking for 3 minutes in 0.5 M Tris/HCl,1.5 M NaCl (pH 7.5) (neutralization). The filters were washed 3 times in standard TTBS and incubated with rhamnogalacturonase-antiserum as described by Burnette (1981). 2×10$^5$ colonies were screened using this procedure, among which 36 positive colonies were identified. Double stranded phagemid DNA was purified from 4 independent colonies that scored positive with rhamnogalacturonase-antiserum, and was characterized further at DNA level.

2.2.2 Sequence analysis of *A. aculeatus* rhgA cDNA clones cDNA inserts were sequenced according to the method of Sanger using the SK primer (Stratagene, La Jolla), the T7 primer (Stratagene, La Jolla) and dedicated synthetic oligonucleotides. The insert of pUR7510 (FIG. 5) was completely sequenced in both directions, and was found to comprise the entire coding region of the rhamnogalacturonase gene (rhgA, FIG. 6, sequence listing no. 5). Regions encoding amino acid sequences corresponding to CNBr fragment #7, CNBr fragment #15, Endolys#5 and Endolys#7 (sequence listing no. 1, no. 2, no. 4 and no. 3 respectively) were encountered within the coding region, positively identifying the cloned cDNA as corresponding to A. aculeatus rhgA. An Escherichia coli DH5α strain containing this plasmid (CBS 238.92) was deposited at the Centraal Bureau voor Schimmelcultures (CBS) in Baarn, the Netherlands, on May 1th 1992.

2.3. Northern analysis of A. aculeatus RNA

A. aculeatus CBS 115.80 was cultured on 1% sucrose medium and shifted to 1% apple pectin as a carbon source as described above. Total RNA was isolated 0, 6 and 24 hr after shifting from sucrose medium to 1% apple pectin using the guanidinium thiocyanate method, essentially as described by Maniatis et al. (1982). 5 µg of each total RNA sample was glyoxylated and subjected to Northern hybridization analysis using the 1.2 kb KpnI fragment of pUR7510 as a probe. A single hybridization signal was obtained with samples isolated at 6 and 24 hr after shifting to pectin, corresponding to a mRNA length of approximately 1500 bp. No signal was detected in RNA isolated from sucrose grown cells. Using rRNA as marker it was concluded that A. aculeatus rhgA mRNA has a length of about 1500 nucleotides. Since the cDNA inserts, constructed from mRNA after induction of rhamnogalacturonase expression, were isolated by cross reactivity with rhamnogalacturonase antibodies after expression of the cNDA library and since the isolated cDNA inserts hybridise with mRNA after induction of rhamnogalacturonase expression, the isolated cDNA inserts represent a part of the nucleotide sequence of the rhgA gene.

2.4 Number of rhgA and related genes in A. aculeatus and A. niger.

The 1.2 kb KpnI fragment of pUR7510, comprising part of the coding region of the A. aculeatus rhgA gene, was labeled according to a standard random primer labeling protocol and used as a probe for Southern hybridization analysis of restriction enzyme digests of A. aculeatus and A. niger N400 (CBS 120.49) genomic DNA, to establish the number of rhgA (or related) genes that are present in the genome of A. aculeatus and A. niger N400. Using standard methods and stringent conditions for hybridization and washing of the blot, the hybrization patterns of the various restriction enzyme digests of A. aculeatus genomic DNA revealed that only a single copy of the rhgA gene is present in the A. aculeatus genome. However, using less stringent conditions at least one related gene was detected in A. aculeatus and at least three related genes in A. niger N400.

2.5. Isolation of the rhgA gene from A. aculeatus genomic DNA

Since the cDNA inserts described above were derived from isolated mRNA, they do not contain possibly occurring introns. In order to isolate the entire DNA sequence encoding rhamnogalacturonase and its expression signals present on the genome, isolated cDNA inserts comprising part of the coding region of the rhgA gene were used as a probe to screen a genomic library of A. aculeatus.

2.5.1 Construction of a genomic library of A. aculeatus DNA

High molecular weight genomic DNA of A. aculeatus CBS 115.80 was isolated as described by De Graaff et al. (1988). It was partially digested with MboI and the fragments were size fractionated on a sucrose gradient before cloning into the BamHI site of lambda-EMBL4 (Karn J. M. et al 1980). The library comprises 2.9×10⁶ independent clones with an insert size range of 8 to 21 kb and was constructed by Clontech Laboratories Inc.

2.5.2 Isolation of lambda clones comprising the A. aculeatus rhgA gene

The obtained library of A. aculeatus genomic DNA in lambda-EMBL4 was screened using the 0.6 kb XhoI fragment of pUR 7510, comprising part of the coding region of the A. aculeatus rhgA gene, as a probe. The fragment was labelled according to a standard random primer labeling protocol. Approximately 20×10³ plaques were tested in duplo (duplicate filters from each plate) according to standard methods (Maniatis et al., 1982) using E.coli LE392 as plating bacteria. The total length of the inserts contained within the analyzed plaques is equivalent to about 16 times the size of the A. aculeatus genome. Hybridization was performed in 6*SSC, 0.5% SDS, 5*Denhardt solution, 20 µg single stranded herring sperm DNA at 65° C. (Maniatis et al, 1982). Filters were washed three times for 15 minutes in 2*SSC, 0.1% SDS at 65° C. Eighteen plaques, which were also found to hybridize with the duplicate set of filters, were subjected to a rescreening procedure. Using standard procedures DNA was isolated from four independent plaques that scored positive in the rescreening procedure.

2.5.3. Physical mapping of genomic k-clones comprising part of the A. aculeatus rhgA gene The inserts of these four positive clones were mapped by Southern hybridization analysis of single and combined digestions with the restriction enzymes BamHI, BglII, EcoRI, HindIII, SalI, SmaI and XhoI using the 1.2 kb KpnI fragment of pUR7510, comprising part of the coding region of the A. aculeatus rhgA gene, as a probe. The fragment was labelled according to a standard random primer labeling protocol. Combination of the resulting data with known locations of the KpnI and SmaI sites within the cDNA sequence (derived from pUR7510) led to the identification of a 3.9 kb BamHI-SalI fragment which comprises the entire A. aculeatus rhgA gene (FIG. 7).

2.5.4. Sequencing the A. aculeatus rhgA gene

The 3.9 kb BamHI-SalI fragment comprising the entire A. aculeatus rhgA gene was subcloned in pBluescript SK+(Stratagene, La Jolla), yielding pUR 7511 (FIG. 8). An Escherichia coli DH5α strain (containing this plasmid (CBS 239.92) was deposited at the Centraal Bureau voor Schimmelcultures (CBS) in Baarn, the Netherlands, on May 1th, 1992. By further mapping of restriction enzyme sites in the insert of pUR7511, a 2.5 kb HindIII fragment comprising the entire coding region of the rhgA gene was identified. The sequence of this fragment was determined by sequencing the entire fragment in both directions according to the method of Sanger, using T3-primer (Stratagene, La Jolla), T7-primer (Stratagene, La Jolla) and dedicated synthetic primers (FIG. 9, sequence listing 7). Additional sequence information for the region upstream of the rhgA gene was also obtained from pUR7511. Comparison of the genomic DNA sequence of the rhgA gene with the cDNA sequence unambiguously identified the position and the size of three introns (FIG. 9, sequence listing 7).

2.6 Isolation of the rhgI and rhgII genes from A. niger genomic DNA 2.6.1 Isolation of lambda clones comprising the A. niger rhgI and rhgII gene The library of A. niger N400 genomic DNA in lambda-EMBL4 (Harmsen et al 1990) was screened using the 2.5 kb HindIII fragment of pUR7511, comprising the coding region of the A. aculeatus rhgA, as a probe. The fragment was labeled according to a standard random primer labeling protocol. Approximately 40×10³ plaques were tested in duplo (duplicate filters from each plate) according to standard methods (Maniatis et al., 1982) using E.coli LE392 as plating bacteria. The total length of the inserts contained within the analyzed plaques is equivalent to about 25 times the size of the A. niger genome. Hybridization was performed in 6*SSC, 0.5% SDS, 5*Denhardt solution, 20 µg/ml single stranded herring sperm DNA at 58° C. (Maniatis et al, 1982). Filters were washed three times for 15 minutes in 2*SSC, 0.1% SDS at 58° C. Eight plaques which were found to hybridize also in the duplicate set of filters, were subjected to a rescreening procedure. Using standard procedures, DNA was isolated from five independent plaques that scored positive in the rescreening procedure.

2.6.2. Physical mapping of genomic k-clones comprising part of the A. niger rhg gene The inserts of these five positive clones were mapped by Southern hybridization analysis of single and combined digestions with the restriction enzymes BamHI, BglII, EcoRI, HindIII, SalI, PstI and HindII using the 2.5 kb HindIII fragment of pUR7511, comprising the coding region of the A. aculeatus rhgA gene, as a probe. The fragment was labelled according to a standard random primer labeling protocol. Analysis of the resulting data revealed two classes of phages (class I and class II) which are distinguished by hybridization intensity and restriction pattern. Four of the five phages that were analysed belong to the stronger hybridyzing class (I), one phage to the less hybridizing class (II). The corresponding genes (respectively rhgI and rhgII) were characterized by restriction enzyme analysis (FIG. 10). Homologies with the A. aculeatus rhgA protein are 80% and 70% for the rhgI and rhgII proteins respectively, as deduced from a 1500 bp part of the coding region, which was sequenced.

2.6.3. Number of rhgI and closely related genes in A. aculeatus and A. niger

A 2.5 kb BamHI- HindIII fragment, comprising the coding region of the A. niger rhgI gene, was labeled according to a standard random primer labeling protocol and used as a probe for Southern hybridization analysis of restriction enzyme digests of A. aculeatus and A. niger N400 genomic DNA, to establish the number of rhgI (or closely related) genes that are present in the genome of A. aculeatus and A. niger N400. Using standard methods and non-stringent conditions for hybridization and washing of the blot, the hybrization patterns of the various restriction enzyme digests of A. aculeatus and A. niger genomic DNA revealed that at least two related genes were detected in A. aculeatus and A. niger (FIG. 11).

EXAMPLE 3

Overproduction of Aspergillus aculeatus rhgA gene in a suitable Aspergillus aculeatus acceptor strain under the control of regulatory elements of the Aspergillus aculeatus rhgA gene In order to construct an A. aculeatus strain which is capable of overproducing rhamnogalacturonase, multiple copies of the A. aculeatus rhgA gene were introduced into a suitable acceptor strain by co-transformation with the A. niger pyrA gene.

3.1 Construction of a suitable A. aculeatus host strain

A. aculeatus NW215 (cspA1, fwnA1, pyrA4) was used as an acceptor strain in transformation experiments. The cspA1 mutation results in short conidiophores and fwnA1 mutation results in yellowish brown spores. The pyrA mutation causes uridine requirement for growth, and is utilized for the introduction of multiple copies of the rhgA gene in cotransformation experiments. For the construction of A. aculeatus NW215, mutations were induced in condiospores of A. aculeatus CBS 115.80 by UV illumination using the method described by Bos (1987). Conidiospore survival varied from 20 to 57% in the different experiments. A subset of mutagenized spores was selected for uridine deficiency using 5-fluoro orotic acid and standard procedures to screen for a pyrA mutation, yielding amongst others A. aculeatus strain NW 212 (pyrA4).

Another subset of mutagenized spores was selected for short conidiophores. A. aculeatus strain NW210 (cspA1), one of the resulting strains, was again mutagenized to obtain colour mutations. A. aculeatus strain NW213 (cspA1, fwnA1), one of the resulting strains producing yellowish brown spores, was again mutagenized and selected for auxotrophic mutations using a standard filtration enrichment procedure (Uitzetter et al., 1986). Several of the resulting mutant strains carried auxotrophic mutations, among which A. aculeatus strain NW214 (cspA1, fwnA1, lysB2) and A. aculeatus strain NM216 (cspA1, fwnA1, lysA1) were identified. Two crosses were performed: 1) A. aculeatus strain NW212 with A. aculeatus strain NM214 and 2) A. aculeatus strain 212 with A. aculeatus strain NW216, using the method described by Bos (1987). From the isolated heterozygous diploid colonies a few spores were streaked directly onto CM-benomyl plates for haploidization. Among the resulting recombinant strains A. aculeatus strain NW215 (cspA1, fwnA1, pyrA4) and A. aculeatus strain NM217 (cspA1, fwnA1, pyrA4, lysA1) were found.

3.2 Co-transformation of A. aculeatus using pyrA as selectable marker

A. aculeatus strain NW215 was co-transformed with mixtures of two different DNA fragments in various ratios using standard techniques (e.g Goosen et al., 1987). The two fragments used were the 3.8 kb XbaI fragment of A. niger N400, comprising the entire A. niger pyrA gene including functional promoter (Goosen et al., 1987), and a 3.9 kb BamHI-SalI fragment of A. aculeatus CBS 115.80, comprising the entire rhgA gene and flanking sequences (FIG. 8). The two plasmids were used in a ratio of 1:20 for pyrA:rhgA.

3.3. Identification and analysis of multicopy transformants

Transformed strains were selected by their ability to grow in the absence of uridine. A selected number of transformants was analysed for cotransformation. They were subsequently grown in a medium containing per liter 1.9 g NH₄Cl, 0.26 g KCl, 0.76 g KH₂PO₄. 0.26 g MgSO₄.7 H₂O ) adjusted to pH 6.0 with KOH, 1% sugar beet pulp and 1 ml of a 1000×concentrated Visniac trace elements solution (Visniac and Santer 1957). Incubation was carried out for 48 hours in 250 ml shake flasks shaking at 30° C. after which the culture was filtrated through miracloth. The culture filtrate was analysed on a SDS-PAGE gelsystem followed by Western blotting as described above. Transformants which had incorporated one or more additional copies of the A. aculeatus rhgA gene were identified by quantitative Western analysis of the culture supernatant using the rhamnogalacturonase-antiserum (FIG. 12). Thus, overproduction of A. aculeatus rhgA was achieved by the introduction of additional copies of the A. aculeatus rhgA gene in the A. aculeatus genome in at least 10 strains of A. aculeatus which paves the way for the production of rhamnogalacturonase at an economically feasible scale. Determination of the copy-number of rhgA genes in two transformants (67 and 75) by Southern analysis revealed that about 5–8 additional copies of the rhgA gene have been introduced in both transformants of *A. aculeatus*. Transformant 75 and the wild type strain were grown in 250 ml shake flasks on minimal medium and 1% sucrose as described above. After 24 hours of incubation 1% apple pectin was added. After another 24 hours the culture was filtered over miracloth and the filtrate was concentrated and analysed for rhamnogalacturonase activity using the DNS method to demonstrate reducing sugars. A three fold increase (OD 0.64 and 1.94 for wild type strain and transformant respectively) in rhamnogalacturonase activity was observed.

These filtrates were also used in a apple mash experiment as described in chapter 1.2.2. Viscosity reduction was measured after 60 minutes of incubation and was 89%, 90.5% and 93% after incubation with Biopectinase LQ, Biopectinase LQ+wild type filtrate and Biopectinase+transformant filtrate respectively. These results clearly show that overproduction of functional rhamnogalacturonase, capable of improving viscosity reduction in hot mash application trials, can be achieved by introduction of additional copies of the *A. aculeatus* rhg gene in the *A. aculeatus* genome.

EXAMPLE 4

Overexpression of the *Aspergillus aculeatus* rhgA gene in Aspergilli controlled by other regulatory elements than those derived from the *Aspergillus aculeatus* rhgA gene To further increase the production level of rhamnogalacturonase, alternative expression systems can be employed. For this purpose the coding part of the rhgA gene can be detached from the upstream control regions (comprising a.o. the promoter), and placed under the control of other promoters derived from Aspergillus strains by fusion at the ATG-translational start signal. Promoters directing the expression of the following genes can be used: the xylanase (xylA) gene of *A. niger var. awamori* CBS 115.52 (xylA promoter), the glucoamylase (glaA) gene of *A. niger* CBS 120.49 (glaA promoter) and the glyceraldehyde-3-phosphatedehydrogenase (gpdA) gene of *A. nidulans* (gpdA promoter).

4.1 xylA promoter

The 3.0 kb KpnI fragment of plasmid pAW14B (described in patent application WO 91/19782, Van Gorcom et al., 1991) was inserted in the KpnI site of pTZ19R, yielding pUR2930 (FIG. 13). This plasmid was used as a template in a first PCR reaction (PCR1) using primer XYLNSI (5'-CGAGGTTGTTCAAGCGT-3', sequence listing no. 9) capable of hybridizing upstream of the NsiI site in the xylA promoter region of pUR2930, and a hybrid primer XYL-RHG (5'-AGAAGGAAAAGAGCACGCATGATGAT-TGAAGAAAGCT-3', sequence listing no. 10) capable of hybridizing just upstream of the ATG-translational start signal of the xylA gene and fusing it to the region of the rhgA gene just downstream of the translational start signal at the ATG codon. In a second PCR reaction (PCR2) using pUR7511 as a template and a primer RHGXYL (5' AGCTTTCTTCAATCATCATGCGT-GCTCTTTTCCTTCT-3', sequence listing no. 11), complementary to XYLRHG, and a primer RHGKPN (5'-ATCAT-GTTCCCACTGGC-3', sequence listing no. 12), capable of hybridizing just downstream of the KpnI site of the *A. aculeatus* rhgA gene, the sequence of the xylA gene immediately upstream of the ATG translational startsignal was fused to the first section of the rhgA gene. The fragments resulting from PCR1 and PCR2 were mixed and subjected to another round of PCR amplification (PCR3). The fragment resulting from PCR3 is digested with NsiI and KpnI and used in a ligation reaction with the 2.4 kb BamHI-NsiI fragment of pUR2930 and the 5.4 kb KpnI-BamHI fragment of pUR7511 (partially digested with KpnI). The resulting plasmid pUR 7512 comprises the *A. aculeatus* rhgA gene fused to the *A. niger var. awamori* xylA promoter at the ATG-translational startsignal (FIG. 14).

This plasmid and suitable fragments thereof can be used together with the 3.8 kb XbaI-fragment of the *A. niger* pyrA gene in co-transformations of *A. aculeatus* strain NW215, essentially as described section 3.2 Transformants with a PYR+ phenotype can be screened for the presence of multiple copies of the rhgA gene by Southern hybridisation analysis, which is facilitated by the differences in the length of fragments generated by restriction enzyme digestions between the native copy of the rhgA gene and the copies behind the xylA promoter that are newly introduced, or by Western analysis of the culture supernatant using the rhamnogalacturonase-antiserum. Alternatively, the amdS gene of *A. nidulans* can be inserted in pUR7512, and used in transformation experiments for selection of transformants containing multiple copies of the rhgA gene. Transformants containing multiple copies of the newly introduced *A. aculeatus* rhgA gene behind the *A. niger var. awamori* promoter can be grown in media that induce increased transcription levels from the xylA promoter, for example media containing wheat bran or xylan as described in patent application WO 91/19782 (Van Gorcom et al., 1991). Similarly, *A. niger* strains containing genetic markers, for example pyrA− routants of *A. niger*. N400 can be used in cotransformations in order to introduce multiple copies of the *A. aculeatus* rhgA gene under the control of the xylA promoter in these strains. Moreover, following the same approach, plasmid pUR7512 and suitable fragments or plasmids derived therefrom, can be used for the introduction of multiple copies of the *A. aculeatus* rhgA gene under the control of the xylA promoter into strains of *A. aculeatus* or other species of the genus Aspergillus, for example *A. oryzae, A. japonicus, A. sojae, A. tubigensis, A. awamori, A. nidulans*, etc.

As a further example a 5.4 kb BamHI-SalI fragment of plasmid pUR7512, comprising the rhgA gene of *A. aculeatus* under the control of the xylA promoter from *A. niger var. awamori* (FIG. 14) was introduced in *A. niger var. awamori* CBS 115.52. To this end a pyrA- variant of *A. niger var. awamori* CBS 115.52 was constructed using UV- mutagenesis and screening on fluoroorotic acid plates (3, 10 E6 spores were irradiated for 90 seconds at 20 erg/mm2/sec with UV radiation, yielding 44% survival). Within the obtained group of pyr- variants two complementation groups could be identified by transformation with the 3.8 kb XbaI fragment of *A. niger* N400, comprising the entire *A. niger* pyrA gene and functional promoter (Goosen et al. 1987). A pyr A- variant of *A. niger var. awamori* CBS 115.52 that could be complemented by the *A. niger* pyr A gene was identified and named strain NW208. Multiple copies of the fusion construct comprising the *A. aculeatus* rhgA gene under the control of the xylA promoter were introduced in this strain by co-transformation of a 5.4 kb BamHI-SalI fragment of plasmid pUR7512 (FIG. 14) comprising the rhgA gene of *A. aculeatus* under the control of the xylA promoter from *A. niger var. awamori* and the 3.8 kb XbaI-fragment of the *A. niger* pyr A gene, essentially as described in chapter 3.2. Six transformants with a pyr A+phenotype were screened on rhamnogalacturonase activity by Western analysis according to the following method: Strains were grown in baffled shake flasks (500 ml) with 200 ml synthetic media (pH 6.5 with KOH) after inoculation with 10 E6 spores/ml. The medium had the following composition (AW medium):

| | |
|---|---|
| sucrose | 10 g/l |
| KCl | 0.52 g/l |
| $MgSO_4.7H_2O$ | 0.49 g/l |
| $ZnSO_4.7H_2O$ | 22 mg/l |
| $MnCl_2.4H_2O$ | 5 mg/l |
| $CaCl_2.6H_2O$ | 1.7 mg/l |
| $NaH_2MoO_4.2H_2O$ | 1.5 mg/l |
| $NaNO_3$ | 6.0 g/l |
| $KH_2PO_4$ | 1.52 g/l |
| Yeast extract | 1.0 g/l |
| $H_3BO_3$ | 11 mg/l |
| $FeSO_4.7H_2O$ | 5 mg/l |
| $CuSO_4.5H_2O$ | 1.6 mg/l |
| $Na_2EDTA$ | 50 mg/l |

Incubation took place at 30° C., 125 rpm for 24 hours in a Mk X incubator shaker. After growth cells were collected by filtration (0.45 μm) washed twice with AW medium without sucrose and yeast extract (salt solution), transferred to 500 ml shake flasks and resuspended in 100 ml salt solution to which xylose was added to a final concentration of 10 g/l (induction medium). After 24 hours biomass was removed by filtration over miracloth and rhamnogalacturonase was detected by Western analysis as described above (FIG. 15). From FIG. 15 it is a clear that rhamnogalacturonase can be efficiently produced in *A. niger var. awamori* using the xylA promoter. Strong overexpression was found in transformants 3 and 5. Activity of *A. aculeatus* rhamnogalacturonase, produced by *A. niger var. awamori* under the control of the xylA promoter, on Modified Hairy Regions was done as described in chapter 1.2.1 (10 μl of filtrate of transformant 3 (see above) added to MHR) and analysed with the Dionex system (FIG. 16). From FIG. 16 it is clear that rhamnogalacturonase produced by *A. niger var. awamori* under the control of the xylA promoter is active on isolated Modified Hairy Regions. Application trials as described in chapter 1.1.2. were performed with Biopectionase LQ (500 g/ton) in the presence and absence of 3 ml of filtrate of *A. niger var awamori* transformant 3, cultured as described above. Juice yield was measured after 2 hours of incubation and a 10% increase in yield at equal brix was observed in the presence of rhamnogalacturonase.

Thus high expression levels of functional *A. aculeatus* rhamnogalacturonase were achieved in *A. niger var. awamori* under the control of the *A. niger var. awamori* xylanase promoter.

4.2 glaA promoter

An approach similar to that outlined in section 4.1 can also be followed for the construction of plasmids in which the *A. aculeatus* rhgA gene has been fused to the promoter of the *A. niger* glaA gene at the ATG-translational startsignal, yielding plasmids essentially as described in patent application WO 91/19782 (Van aGorcom et al., 1991). In this case pAN52-6 (Van den Hondel et al, 1991) can be used as a template in PCR reactions providing the functional glaA promoter.

The resulting plasmids or suitable fragments thereof can be used to generate transformants containing multiple copies of the *A. aculeatus* rhgA gene under the control of the *A. niger* glaA promoter in strains of species of the genus Aspergillus carrying genetic markers, essentially as outlined in section 4.1 of this example.

4.3 gpdA promoter

An approach similar to that outlined in section 4.1 can also be followed for the construction of plasmids in which the *A. aculeatus* rhgA gene is fused to the promoter of the *A. nidulans* gpdA gene at the ATG-translational startsignal, yielding plasmids essentially as described in patent application WO 91/19782 (Van Gorcom et al., 1991). For this purpose pAN52-1 (Punt et al., 1987) can be used as a template in PCR reactions to generate a fragment comprising the gpdA promoter sequences up to the ATG-translational startsignal fused to the rhgA coding region. The resulting plasmids or suitable fragments thereof can be used to generate transformants containing multiple copies of the *A. aculeatus* rhgA gene under the control of the *A. nidulans* gpdA promoter in strains of species of the genus Aspergillus carrying genetic markers, essentially as outlined in section 1. of this example.

EXAMPLE 5

Production of *Aspergillus aculeatus* rhamnogalacturonase in yeast 5.1 Introduction For the production of *A. aculeatus* rhamnogalacturonase in yeasts, vectors can be constructed in which the sequences encoding the mature *Aspergillus aculeatus* rhamnogalacturonase protein are fused to yeast regulatory sequences for the transcription of the gene. If secretion of the rhamnogalacturonase protein is desired, functional yeast signal sequences can be added to the coding sequence of the rhgA gene. Since yeasts may not be capable of correct removal of the introns from the primary RNA transcript of the *A. aculeatus* rhgA gene, the introns should not be present in these constructions. The cDNA fragment of the rhgA gene, present in pUR7510, can serve as a base for such constructions.

Efficient production and secretion by yeast of an Aspergillus gene was previously described for the xylanase gene of *Aspergillus niger var. awamori* in patent application WO 91/19782 (Van Gorcom et al., 1991). Production and secretion of the xylanase was achieved by fusion of the promoter from the *Saccharomyces cerevisiae* GAL7 gene, and the signal sequence of the *Saccharomyces cerevisiae* SUC2 gene encoding the invertase protein, to the mature xylanase gene from which the intron was correctly removed. Production of the *Aspergillus aculeatus* rhamnogalacturonase protein in yeast can be accomplished by a functional fusion of the GAL7-promoter and invertase signal sequence from yeast to the mature, intronless, rhgA gene. Such constructions can be incorporated in either autonomously replicating yeast vectors, or alternatively, in yeast vectors that are capable of integration in the yeast genome in single or multiple copies. The levels of expression of the *A. aculeatus* rhgA gene directed by such constrictions can be further improved by adjustment of the codon usage of the *A. aculeatus* rhgA gene according to the codon preferences known for yeasts.

5.2 Expression in *Saccharomyces cerevisiae* of the rhamnogalacturonase protein using autonomously replicating vectors The expression plasmid pUR2904 (FIG. 17), used for the secretion of the *Aspergillus niger var. awamori* xylanase protein by *Saccharomyces cerevisiae* (Van Gorcom et al., 1991), can serve as basis for the expression of the *A. aculeatus* rhamnogalacturonase protein in yeast. pUR2904 is an *E. coli-S. cerevisiae* shuttle plasmid which contains a correct fusion of the coding sequences of the *S. cerevisiae* invertase signal sequence and the mature *A. awamori* xylanase, under control of the promoter sequences of the *S. cerevisiae* GAL7-gene. Furthermore, this plasmid contains the replication origin of the yeast 2-micron plasmid, the *S. cerevisiae* LEU2-gene, and the SalI-EcoRI fragment of pBR322 containing the ampicillin resistance gene and the MB1 replication origin.

The sequences coding for the mature rhamnogalacturonase protein, as present in pUR7510, can be fused to the GAL7-promoter and invertase signal sequence, as present in pUR2904, by using the same approach as described for the fusion of the rhgA gene to the xylA promoter in section 4.1. Here, pUR2904 can be used as a template in a first PCR experiment using primer GALBGL (5'-GAAGTTA-GATCTAGCTATACT-3', sequence listing no. 13) capable of hybridizing at the beginning of the GAL7-promoter on the BglII-site, and primer INVRHG (5'-CAACACTGCCA-GAGAGTTGCGCAGATATTTTGGCTGCAA-3', sequence listing no. 14) serving the correct fusion of the invertase signal sequence to the mature rhamnogalacturonase protein. In a second PCR experiment pUR7510 can be used as a template using primer RHGINV (5'-TTGCAGC-CAAAATATCTGCGCAACTCTCTGGCAGTGTTG-3', sequence listing no. 15), complementary to INVRHG, and primer RHGEND (5'-CCCAAGCTTCAATCAACTAC-TAGCCTGCCAAGGCA-3', sequence listing no. 16) capable of hybridizing to the end of the coding sequence of the rhgA gene, and adding additional translational stopcodons and a HindIII-site to the 3' end of it. In the third PCR-experiment the two products are fused and after digestion with BglII and HindIII the 1662 bp fragment can be ligated to DglII—HindIII digested pUR2904 resulting in plasmid pUR7513 (FIG. 18). Plasmid pUR7513 will then contain the signal sequence of the *Saccharomyces cerevisiae* invertase, correctly fused to the coding sequences of the mature *Aspergillus aculeatus* rhamnogalacturonase protein, under transcriptional control of the *Saccharomyces cerevisiae* GAL7 promoter sequences. Expression of the rhamnogalacturonase protein by yeast can then be achieved by transformation of a suitable *S. cerevisiae* strain with pUR2913, and growing leu+transformants in media containing galactose as a carbon source.

REFERENCES

Voragen A. G. J. (1989): Food enzymes: Prospects and limitations. In: Roozen J. P., Rombouts F. M., Voragen A. G. J. (eds): Food Science: Basic research for Technological Progress. PUDOC, Wageningen, The Netherlands.

Voragen A. G. J., Beldman G. (1990) Enzymatische modificatie van polysacchariden. VMT (12): 23–27.

McNeil M., Darvill A. G., Fry SC, Albersheim P. (1984) Ann. Rev. Biochem. (53) 625–636

Pilnik (1982). in: Dupuy P (ed) Use of enzymes in the beverage industry. Technique et documentation, Lavoisier, Paris Renard C. M. G. C., Voragen A. G. J., Schols H. A., Searle-van Leeuwen M. J. F., Thibault J. F., Pilnik W (1989) Apple protopectin: Preliminary study of enzymatic extraction. In: Roozen J. P., Rombouts F. M., Voragen A. G. J. (eds): Food Science: Basic research for Technological Progress. PUDOC, Wageningen, The Netherlands.

Ishii S., Yokotsuka T., (1973) Suspectibility of fruit juice to enzymatic clarification by pectin lyase and its relation to pectin in fruit juice. J. Agric. Food Chem. (20): 265–272

Maldonando M. C., Strasser de Saad A. M., Callieri D (1989) Catabolite repression of the synthesis of inducible polygalacturonases and pectinesterases by *Aspergillus niger sp*. Current microbiology (18) 303–306

Schols H. A., Geraeds C. C. J. M., Searle-van Leeuwen M. F., Kormelink F. J. M., Voragen A. G. J. (1990a) Rhamnogalacturonase: a novel enzyme that degrades the hairy regions of pectins. Carbohydrate Research (206) 105–115

Schols H. A., Posthumus M. A., Voragen A. J. G. (1990b) Structural features of hairy regions of pectins isolated from apple juice produced by the liquefaction process. Carbohydrate Research (206) 117–129

Colquhoun I. J. (1990) Identification by N. M. R. spectroscopy of oligosaccharides obtained by treatment of the hairy regions of apple pectin with rhamnogalacturonase. Carbohydrate Research (206) 131–144

Veen van der P., Flipphi M. J. A., Voragen A. G. J., Visser J. (1991) Induction, purification and characterisation of arabinases produced by Aspergillus niger. Arch. Microbiol. (157) 23–28

Visniac W., Santer M. (1957) Bacteriol. Rev. (21) 195–237

Burnette W. N. (1981) "Western blotting": Electrophoretic transfer of proteins from Sodium Dodecyl Polyacrylamide gels to unmodified nitrocellulose and radiographic detection with antibody and radioiodinated protein A. Anal.Biochem. (112): 195–203

Aitken, A., M. J. Geisow, J. B. C. Findlay, C. Holmes and A. Yarwood. Peptide preparation and characterization. In: Protein sequencing, a practical approach. J. B. C. Findlay and M. J. Geisow (Eds), IRL press, Oxford. pp43–68

Maniatis T., Frisch E. F., Sambrook J. (1982) Molecular cloning: a laboratory manual. Cold Spring Harbor Laboratory, Cold Spring Harbor, N.Y.

Huse W. D., Hansen C. (1988) Strategies (1) 1–3

De Graaff, L. H., H. W. J. van den Broek and J. Visser (1988). Isolation and expression of the *Aspergillus nidulans* pyruvate kinase gene. Curr. Genet. (13): 315–321

Karn J., Brenner S, Barnett L and Cesareni G (1980). Novel bacteriophage lambda cloning vector. Proceedings of the National Academy of Sciences 77 (9), 5172–5176

Harmsen J. A. M., Kusters-van Someren M. A., Visser J (1990) Cloning and expression of a second *Aspergillus niger* pectin lyase gene (pelA): Indications of a pectin lyase gene family in *A. niger*. Curr. Genet. 18:161–166

Bos C. J. (1987) Induction and isolation of mutants in fungi at low mutagen doses. Curr. Genet (12):471–474

Uitzetter J. H. A. A., Bos C. J., Visser J. (1986) Characterization of *Aspergillus nidulans* mutants in carbon metabolism isolated after D-galacturonate enrichment. J. Gen Microbiol. (132): 1167–1172

Goosen T., Bloemheuvel G., Gysler C., de Bie D. A., van den Broek H. W. J., Swart K (1987) Transformation of *Aspergillus niger* using the homologous orotidine-5'-phosphate-decarboxylase gene. Curr. Genet (11):499–503.

Van Gorcom, R. F. M., Hessing J. G. M., Maat J., Roza M., Verbakel J (1991) Xylanase production. Patent application WO 91/19782

Van den Hondel, C. A. M. J. J., Punt P. J., van Gorcom R. F. M. (1991). Heterologous gene expression in filamentous fungi. In: More Gene Manipulations, J. W. Bennett and L. L. Lasure (Ed), Academic Press, Inc., San Diego.

Punt, P. J., Oliver R. P., Dingemanse M. A., Pouwels P. H., van den Hondel C. A. M. J. J. (1987). Transformation of Aspergillus based on the hygromycin B resistance marker from *Escherichia coli*. Gene (56):117–124.

We claim:

1. A method of detecting a ripening form of a polypeptide which cross reacts with an antibody which specifically binds to an antigenic determinant of rhamnogalacturonase comprising the steps of:

adding said antibody to a sample containing said polypeptide;

incubating said antibody with said sample such that said antibody binds to said polypeptide; and detecting the presence of said polypeptide bound to said antibody.

2. A method of detecting an organism which produces or secretes a polypeptide which cross reacts with an antibody which specifically binds to an antigenic determinant of rhamnogalacturonase comprising the steps of:

incubating the antibody with an organism suspected of producing or secreting said polypeptide under detecting said organism by determining the presence of said conditions whereby said polypeptide binds to said antibody; and polypeptide bound to said antibody.

3. A method of isolating a ripening form of a polypeptide which cross reacts with an antibody which specifically binds to an antigenic determinant of rhamnogalacturonase comprising the steps of:

adding the antibody to a sample containing said polypeptide;

incubating said antibody with said sample such that said antibody binds to said polypeptide; and isolating said polypeptide.

4. A method of isolating an organism which produces or secretes a polypeptide which cross reacts with an antibody which specifically binds to an antigenic determinant of rhamnogalacturonase comprising the steps of:

incubating the antibody with an organism suspected of producing or secreting said polypeptide under conditions whereby said polypeptide binds to said antibody;

detecting the presence of said polypeptide bound to said antibody; and isolating said organism.

\* \* \* \* \*